United States Patent
Robertson et al.

(10) Patent No.: US 11,324,869 B2
(45) Date of Patent: May 10, 2022

(54) DIALYSIS SYSTEMS AND METHODS FOR MODULATING FLOW OF A DIALYSATE DURING DIALYSIS USING RAMAN SPECTROSCOPY

(71) Applicant: Virginia Tech Intellectual Properties, Inc., Blacksburg, VA (US)

(72) Inventors: John L. Robertson, Floyd, VA (US); Ryan Senger, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 17/434,294

(22) PCT Filed: Feb. 26, 2020

(86) PCT No.: PCT/US2020/019964
§ 371 (c)(1),
(2) Date: Aug. 26, 2021

(87) PCT Pub. No.: WO2020/176663
PCT Pub. Date: Sep. 3, 2020

(65) Prior Publication Data
US 2022/0040390 A1 Feb. 10, 2022

Related U.S. Application Data

(60) Provisional application No. 62/810,820, filed on Feb. 26, 2019, provisional application No. 62/810,836, filed on Feb. 26, 2019.

(51) Int. Cl.
*A61M 1/16* (2006.01)
*G01N 21/65* (2006.01)

(52) U.S. Cl.
CPC ........ *A61M 1/1619* (2014.02); *A61M 1/1609* (2014.02); *G01N 21/65* (2013.01);
(Continued)

(58) Field of Classification Search
CPC .............. A61M 1/1619; A61M 1/1609; A61M 2205/3306; A61M 2205/3334; A61M 2205/50; A61M 2230/20; G01N 21/65
See application file for complete search history.

(56) References Cited

U.S. PATENT DOCUMENTS 3,598,727 A  8/1971  Willock
4,172,033 A  10/1979  Willock
(Continued)

FOREIGN PATENT DOCUMENTS

WO  2012140022 A1  10/2012
WO  2015164620 A1  10/2015
WO  2020176663 A1  9/2020

OTHER PUBLICATIONS (Robertson, John et al.) Co-Pending U.S. Appl. No. 17/146,301, filed Jan. 11, 2021, Specification, claims, figures.
(Continued)

*Primary Examiner* — John Kim
(74) *Attorney, Agent, or Firm* — New River Valley IP Law, P.C.; Michele L. Mayberry

(57) ABSTRACT

The present invention is a system to continuously monitor, in real-time, the small molecules being dialyzed during hemodialysis treatment using Raman spectroscopy and press control algorithms. By monitoring the treatment, the amount of water needed per dialysis treatment is drastically reduced by optimizing analyte saturation and removal of wastes. This will significantly conserve water and reduce the cost of dialysis treatments, possibly reducing the amount of time necessary for dialysis treatment, improving quality of life for patients during and after treatment, and reducing the costs of building new treatment centers as well as operating costs.

20 Claims, 36 Drawing Sheets

(52) U.S. Cl.
CPC ............... *A61M 2205/3306* (2013.01); *A61M 2205/3334* (2013.01); *A61M 2205/50* (2013.01); *A61M 2230/20* (2013.01)

(56) References Cited

U.S. PATENT DOCUMENTS

| | | | |
|---|---|---|---|
| 4,267,040 | A | 5/1981 | Schal |
| 4,769,134 | A | 9/1988 | Allan et al. |
| 5,112,127 | A | 5/1992 | Carrabba et al. |
| 5,507,723 | A | 4/1996 | Keshaviah |
| 5,534,997 | A | 7/1996 | Schrader |
| 5,553,616 | A | 9/1996 | Ham et al. |
| 5,786,893 | A | 7/1998 | Fink et al. |
| 6,100,975 | A | 8/2000 | Smith et al. |
| 6,151,522 | A | 11/2000 | Alfano et al. |
| 6,284,131 | B1 | 9/2001 | Hogard et al. |
| 7,326,576 | B2 | 2/2008 | Womble et al. |
| 7,505,128 | B2 | 3/2009 | Zribi et al. |
| 7,524,671 | B2 | 4/2009 | Clarke et al. |
| 7,651,851 | B2 | 1/2010 | Clarke et al. |
| 8,133,194 | B2 | 3/2012 | Szamosfalvi et al. |
| 8,638,431 | B2 | 1/2014 | Ashok et al. |
| 8,699,020 | B1 | 4/2014 | Zhou et al. |
| 8,945,936 | B2 | 2/2015 | Ash et al. |
| 8,953,159 | B2 | 2/2015 | Cunningham et al. |
| 9,089,126 | B2 | 7/2015 | Faulkner et al. |
| 9,215,985 | B2 | 12/2015 | Gross et al. |
| 9,267,845 | B2 | 2/2016 | Ichijyo et al. |
| 9,550,020 | B2 | 1/2017 | Kelly et al. |
| 9,713,666 | B2 | 7/2017 | Pudil et al. |
| 2006/0281068 | A1 | 12/2006 | Maier et al. |
| 2007/0109535 | A1 | 5/2007 | Maier et al. |
| 2008/0097272 | A1 | 4/2008 | Daniel et al. |
| 2008/0158544 | A1 | 7/2008 | Womble et al. |
| 2010/0070197 | A1 | 3/2010 | Wang et al. |
| 2010/0165324 | A1 | 7/2010 | Womble et al. |
| 2012/0008130 | A9 | 1/2012 | Munger et al. |
| 2012/0099102 | A1 | 4/2012 | Bello |
| 2012/0276549 | A1 | 11/2012 | Cunningham et al. |
| 2013/0056418 | A1 | 3/2013 | Kopperschmidt et al. |
| 2014/0052386 | A1 | 2/2014 | Guenther et al. |
| 2014/0098359 | A1 | 4/2014 | Gross et al. |
| 2017/0045455 | A1 | 2/2017 | Robertson et al. |
| 2021/0215610 | A1 | 7/2021 | Robertson et al. |
| 2021/0270742 | A1 | 9/2021 | Senger et al. |

OTHER PUBLICATIONS (Robertson, John L. et al) Co-pending International Application No. PCT/US20/19964, filed Feb. 26, 2020, Specification, Claims, Figures.
(Robertson, John L. et al.) Co-pending U.S. Appl. No. 15/305,940, filed Oct. 21, 2016, Specification, Claims, and Figures.
(Robertson, John L. et al.) PCT Application No. PCT/US2015/027323, filed Apr. 23, 2015 and published as WO2015164620 on Oct. 29, 2015, Specification, Claims, Figures.
Centers for Disease Control and Prevention, National Chronic Kidney Disease Factsheet, 2014, 4 pages.
Collins, AJ et al., "Death, hospitalization, and economic associations among incident hemodialysis patients with hematocrit values of 36 to 39%," J Am Soc Nephrol 12(11):2465-73, 2001.
Co-pending U.S. Appl. No. 15/305,940, Final Office Action dated Jul. 13, 2020, 22 pages.
Co-pending U.S. Appl. No. 15/305,940, Non-Final Office Action dated May 7, 2021, 24 pages.
Co-pending U.S. Appl. No. 15/305,940, Non-Final Office Action dated Nov. 1, 2019, 16 pages.
Co-pending U.S. Appl. No. 15/305,940, Response to Jul. 13, 2020 Final Office Action, filed Oct. 13, 2020, 11 pages.
Co-pending U.S. Appl. No. 15/305,940, Response to Mar. 27, 2019 Restriction Requirement, filed Sep. 27, 2019, 9 pages.
Co-pending U.S. Appl. No. 15/305,940, Response to May 7, 2021 Non-Final Office Action, filed Sep. 7, 2021, 14 pages.
Co-pending U.S. Appl. No. 15/305,940, Response to Nov. 1, 2019 Non-Final Office Action, filed May 1, 2020, 13 pages.
Co-pending U.S. Appl. No. 15/305,940, Restriction Requirement dated Mar. 27, 2019, 9 pages.
Daugirdas, John T. et al. "Improved equation for estimating single-pool Kt/V at higher dialysis frequencies", Nephrol Dial Transplant (2013) 28: 2156-2160.
Daugirdas, John T. et al. "Surface-Area-Normalized Kt/V: A Method of Rescaling Dialysis Dose to Body Surface Area-Implications for Different-Size Patients by Gender", Semin Dial. 2008; 21(5): 415-421, 17 pages.
Dobre, M, Meyer, TW, Hostetter, TH, "Searching for uremic toxins," Clin J Am Soc Nephrol 8: 322-327, 2013.
Duranton, F et al., "Normal and pathological concentrations of uremic toxins," J Am Soc Nephrol 23: 1258-1270, 2012.
Eknoyan, G. et al., "Effects of dialysis dose and membrane flux in maintenance hemodialysis," New Engl Journ Med 347: 2010-2019, 2002.
Ito, S, Yoshida, M, "Review: Protein-bound uremic toxins: new culprits of cardiovascular events in chronic kidney disease patients," Toxins 6: 665-678, 2014; doi:I0.3390/toxins6020665.
Jaejin Kim et al., "Feasibility Study for the Monitoring of Ureain Dialysate Solution using Raman Spectroscopy", Bull. Korean Chem. Soc 2011, vol. 32, No. 3 805-808.
Jha, V. et al., "Chronic kidney disease: global dimension and perspectives", The Lancet, 2013, 382(9888), 260-272.
Levey, AS et al., "Controlling the epidemic of cardiovascular disease in chronic renal disease: What do we need to learn? Where do we go from here?," Amer J Kid Disease 32: 853-906, 1998.
Liabeuf, S, Drukke, TB, Massay, ZA, "Protein-bound uremic toxins: new insight from clinical studies," Toxins 3: 911-919, 2011.
Meyer, TW, Hostetter, TH, "Uremia", New Engl J Med 357: 1316-1325, 2007.
Minka "A statistical learning/pattern recognition glossary." Retrieved Jun. 29, 2005: 2008. Available online http://alumni.media.mit.edu/~tpminka/statlearn/glossary/glossary.htm , accessed Jul. 1, 2020 (Year: 2005).
PCT Application No. PCT/US2015/027323 International Search Report and Written Opinion dated Sep. 8, 2015, 11 pages.
Vanholder, R, et al., European Uremic Toxin Work Group (EUTox), "Review on uremic toxins: classification, concentration, and interindividual variability," Kidney Int. May 2003;63(5):1934-43, 2003.
Pending International Application No. PCT/US20/19964, International Search Report and Written Opinion dated May 22, 2020, 7 pages.
Shinzawa, H. et al., "Multivariate data analysis for Raman spectroscopic imaging" Journal of Raman Spectroscopy, 2009, 40:1720-1725.
Shusterman, V. et al. "Enhancing the precision of ECG baseline correction: selective filtering and removal of residual error". Comput. Biomed. Res. 2000. 33(2): 144-160, Abstract only.
Stellman, C.M. et al. "Multivariate Raman Imaging of Simulated and Real World Glass-Reinforced Composites". Appl. Spectrosc. 1996. 50: 552-557, Abstract only.
Wang, N. et al. "Recent advances in spontaneous Raman spectroscopic imaging: Instrumentation and applications" Current Medicinal Chemistry, vol. 27, No. 36, 2020, pp. 6188-6207(20), Available online Jul. 26, 2019, Abstract only.
Ward, R. A. et al., "Dialysate Flow Rate and Delivered Kt/Vurea for Dialyzers with Enhanced Dialysate Flow Distribution", Clin J Am Soc Nephrol 6: 2235-2239, Sep. 2011.
Yang, Y.T. et al., Off-Resonance SERS Nanoprobe-Targeted Screen of Biomarkers for Antigens Recognition of Bladder Normal and Aggressive Cancer Cells. Analytical Chemistry 2019;91(13): 8213-8220.
Zhang, D. and Ben-Amotz, D. "Enhanced Chemical Classification of Raman Images in the Presence of Strong Fluorescence Interference". Appl. Spectrosc. OSA, 2000, 54(9): 1379-1383, Abstract only.

(56) References Cited

OTHER PUBLICATIONS

Zhao, J. et al. "Automated autofluorescence background subtraction algorithm for biomedical Raman spectroscopy". Appl. Spectrosc. 2007. 61(11): 1225-1232, Abstract only.

Zu, T.N.K. et al., Assessment of ex vivo Perfused Liver Health by Raman Spectroscopy. J Raman Spectrosc. 2015; 46: 551-558, Abstract only.

Zu, T.N.K. et al., Near-Real-Time Analysis of the Phenotypic Responses of Escherichia coli to 1-Butanol Exposure Using Raman Spectroscopy. J Bacteriol. 2014;196: 3983-3991.

(Robertson, John L. et al.) Co-pending U.S. Appl. No. 17/345,735, filed Jun. 11, 2021, specification, Claims, and Figures.

(Senger, R. et al.) Co-Pending U.S. Appl. No. 17/188,737, filed Mar. 1, 2021, Specification, Drawings, and Claims.

Afseth, N.K. and Kohler, A. "Extended multiplicative signal correction in vibrational spectroscopy, a tutorial". Chemometrics and Intelligent Laboratory Systems. 2012. 117: 92-99. 10.1016/j.chemolab. 2012.03.004, Abstract only.

Athamneh, A.I.M. and Senger R.S. Peptide-Guided Surface-Enhanced Raman Scattering Probes for Localized Cell Composition Analysis. Appl Env Microbiol. 2012;78:7805-7808.

Athamneh, A.I.M. et al., Phenotypic Profiling of Antibiotic Response Signatures in Escherichia coli Using Raman Spectroscopy. Antimicrob Agents Chemother. 2014;58:1302-1314.

Balan et al. "Vibrational spectroscopy fingerprinting in medicine: from molecular to clinical practice." Materials 12.18 (2019): 2884, 40 pages.

Beattie, J.R. and McGarvey, J.J. "Estimation of signal backgrounds on multivariate loadings improves model generation in face of complex variation in backgrounds and constituents". J of Raman Spectrosc. 2013. 44(2): 329-338. 10.1002/jrs.4178, Abstract only.

Bird, B. et al., Cytology by Infrared Micro-Spectroscopy: Automatic Distinction of Cell Types in Urinary Cytology. Vib Spectrosc. 2008;48: 101-106, 15 pages.

Bouatra, S. et. al. The Human Urine Metabolome. PLoS One. 2013;8: e73076, 25 pages.

Cai, T.T. et al. "Enhanced Chemical Classification of Raman Images Using Multiresolution Wavelet Transformation". Appl. Spectrosc. 2001. 55(9): 1124-1130.

Cai, Y. et al. "Baseline correction for Raman spectra using penalized spline smoothing based on vector tansformation". Anal. Methods. 2018. 10(28): 3525-3533, Abstract only.

Candeloro, P. et al. "Raman database of amino adds solutions: A critical study of extended multiplicative signal correction". Analyst. 2013.138(24): 7331-7340).

Canetta, E. et al., Modulated Raman spectroscopy for enhanced identification of bladder tumor cells in urine samples. J Biomed Opt. 2011;16(3): 037002, 8 pages.

Chen, D. et al. "Adaptive wavelet transform suppresses background and noise for quantitative analysis by Raman spectrometry". Anal. Bioanal. Chem. 2011. 400(2): 625-634, Abstract Only.

Chiu, Y.C. et al., Enhanced Raman sensitivity and magnetic separation for urolithiasis detection using phosphonic acid-terminated Fe3O4 nanoclusters. J. Mater. Chem. B 2015(3):4282-4290.

Co-Pending U.S. Appl. No. 15/305,940, Final Office Action dated Dec. 1, 2021, 27 pages.

Das, R.S. and Agrawal, Y.K. "Raman spectroscopy: Recent advancements, techniques and applications". Vib. Spectrosc. 2011. 57(2): 163-176, Abstract only.

Depciuch, J. et al. "Application of Raman Spectroscopy and Infrared Spectroscopy in the Identification of Breast Cancer". Appl. Spectrosc. 2016. 70(2): 251-263.

Eilers, P.H.C. "A perfect smoother". Anal. Chem. 2003. 75(14): 3631-3636, Abstract only.

Fisher, A.K. et al. "The RametrixTM LITE Toolbox v1.0 for MathLab®". J. Raman Spectrosc. 2018, 49(5): 885-896, Abstract only.

Gautam, R. et al. "Review of multidimensional data processing approaches for Raman and infrared spectroscopy". EPJ Techn. Instrum. 2015. 2(1): 8, 38 pages.

He, S. et al. "Baseline correction for Raman spectra using an improved asymmetric least squares method". Anal. Methods. The Royal Society of Chemistry, 2014. 6(12): 4402-4407.

Huttanus, H. et al. "Raman Chemometric Urinalysis (Rametrix™) as a screen for bladder cancer," PLoS One. 2020; 15(8): e0237070. Published online Aug. 21, 2020.

Hyde, F.W. et al., "Detection of antigens in urine of mice and humans infected with Borrelia burgdorferi, etiologic agent of Lyme disease," J Clin Microbiol 27, 58-61 (1989).

Kerr, L.T. et al., Methodologies for bladder cancer detection with Raman based urine cytology. Analytical Methods, 2016;8: 4991-5000, Abstract only.

Lee, S. et al., "Improving Clearance for Renal Replacement Therapy", Kidney 360 Publish Ahead of Print, published May 12, 2021, 32 pages.

Li, J. et al. "Wavelet transform based on the optimal wavelet pairs for tunable diode laser absorption spectroscopy signal processing". Appl. Spectrosc. 2015. 69(4): 496-506.

Lieber, C.A. and Mahadevan-Jansen, A. "Automated Method for Subtraction of Fluorescence from Biological Raman Spectra". Appl. Spectrosc. 2003. 57: 1363-1367, Abstract only.

Liland, K. et al. "Model-based pre-processing in Raman spectroscopy of biological samples". J. Raman Spectrosc. 2016. 47(6): 643-650.

Liland, K. et al. "Optimal Choice of Baseline Correction for Multivariate Calibration of Spectra" Appl. Spectrosc. 2010, 64: 1007-1016.

Liu, J. et al. "Goldindec: A Novel Algorithm for Raman Spectrum Baseline Correction". Appl. Spectrosc. 2015. 69(7): 834-842.

Lo, P.A. et al., Automatic Raman spectroscopic urine crystal identification system using fluorescent image-guided 2D scanning platform with Fe3O4 crystal violet nanoclusters. J Raman Spectrosc 2018;50(1)34-50, Abstract only.

Magni, R. et al., "Application of Nanotrap technology for high sensitivity measurement of urinary outer surface protein A carboxyl terminus domain in early stage Lyme borreliosis," J Transl Med (2015) 13:346, 22 pages.

Mahadevan-Jansen, A. and Richards-Kortum, R.R. "Raman spectroscopy for the detection of cancers and precancers". J. Biomed. Opt. 1996. 1(1): 31-70.

Martens, H. and Stark, E. "Extended multiplicative signal correction and spectral interference subtraction: new preprocessing methods for near infrared spectroscopy." J. Pharm. Biomed. Anal. 1991. 9 8: 625-635, Abstract only.

Mazet, V. et al. "Background removal from spectra by designing and minimising a non-quadratic cost function". Chemom. Intell. Lab. Syst. 2005. 76(2): 121-133.

Meyer, T. W. et al., "Dialysis Cannot be Dosed", Semin Dial. 2011; 24(5): 471-479, 19 pages.

Mosier-Boss, P.A. et al. "Fluorescence rejection in Raman spectroscopy by shifted-spectra, edge detection, and FFT filtering techniques". Appl. Spectrosc. 1995. 49: 630-638.

Movasaghi, Z. et al., Raman Spectroscopy of Biological Tissues. Appl Spectrosc Rev. 2007;42: 493-541.

Pegalajar-Jurado, A. et al., (2018) "Identification of urine metabolites as biomarkers of early Lyme Disease," Mature Scientific Reports 8:12204, 12 pages.

Peng, J. et al. "Asymmetric least squares for multiple spectra baseline correction". Anal. Chim. Acta. 2010. 683(1): 63-68.

Rauter, C. et al., "Critical evaluation of urine-based PCR assay for diagnosis of Lyme borreliosis," Clin Diagn Lab Immunol 12: 910-917 (2005).

Scholtes-Timmerman, M. et al. "A novel approach to correct variations in Raman spectra due to photo-bleachable cellular components". Analyst. 2009. 134(2): 387-393.

Schulze, G. et al. "Investigation of selected baseline removal techniques as candidates for automated implementation". Appl. Spectrosc. 2005. 59(5): 545-574.

Senger, R.S. and Robertson, J.L. "The RametrixTM PRO Toolbox v1.0 for MatLab®". PeerJ. 2020. 8: e8179.

Senger, R.S. et al. "Spectral characteristics of urine from patients with end-stage kidney disease analyzed using Raman Chemometric Urinalysis (Rametrix)". PLoS One. 2020. 15(1): e0227281).

(56) References Cited

OTHER PUBLICATIONS

Senger, R.S. et al. "Spectral characteristics of urine specimens from healthy human volunteers analyzed using Raman chemometric urinalysis (Rametrix)". PLoS One. 2019. 14(9): e0222115.

Senger, R.S., Kavuru, V., Sullivan, M., Gouldin, A., Lundgren, S., Merrifield, K. (2019), Spectral characteristics of urine specimens from healthy human volunteers analyzed using Raman chemometric urinalysis (Rametrix). PLoS One 14(9): e0222115.

Senger, R.S., Sullivan, M., Gouldin, A., Lundgren, S., Merrifield, K., Steen, C., Spectral characteristics of urine from patients with end-stage kidney disease analyzed using Raman Chemometric Urinalysis (Rametrix) PLoS One 15(1): e0227281, 2020.

Shapiro, A. et al., Raman molecular imaging: a novel spectroscopic technique for diagnosis of bladder cancer in urine specimens. Eur Urol. 2011;59: 106-112.

Co-Pending U.S. Appl. No. 15/305,940, Response to Dec. 1, 2021 Final Office Action, dated Feb. 25, 2022, 17 pages.

Co-Pending U.S. Appl. No. 15/305,940, Applicant-Initiated Interview Summary dated Mar. 28, 2022, 3 pages.

DIALYSIS SYSTEMS AND METHODS FOR MODULATING FLOW OF A DIALYSATE DURING DIALYSIS USING RAMAN SPECTROSCOPY

CROSS-REFERENCE TO RELATED APPLICATIONS

The present application is a National Stage application under 35 U.S.C. § 371 of International Application No. PCT/US20/19964 filed Feb. 26, 2020, which application relies on and claims priority to and the benefit of the filing date of U.S. Provisional Patent Application No. 62/810,820, filed Feb. 26, 2019 and of U.S. Provisional Patent Application No. 62/810,836, filed Feb. 26, 2019. The entire disclosures of which are hereby incorporated herein by reference.

BACKGROUND OF THE INVENTION

Field of the Invention

Hemodialysis is a treatment option for patients with kidney failure that helps to remove metabolic wastes from the blood when the kidneys are not functioning properly. During hemodialysis, blood is drawn from the patient and is then sent into a dialyzer coil, where only small molecules are permitted to pass through the selectively permeable membrane and then accumulate in an aqueous phase (called dialysate). The dialysate, along with metabolic wastes, are then discarded down the drain and the cleansed blood is returned to the patient. The dialysate solution consists of ultra-purified water (ions or contaminants can be harmful to the patients), which is then buffered with bicarbonate. Some research indicates that the amount of dialysate currently being used for hemodialysis treatments may be much larger than what is required, since waste dialysate is rarely saturated to capacity with wastes during a standard four-hour treatment time. Standard hemodialysis treatments are administered three times weekly for a standard four hours no matter the age, weight, or health of the patient. Each treatment consumes an average of 120 liters of ultra-purified water per treatment.

Dialysis centers generally produce their own dialysate—due to the volume of dialysate they use—and it is more feasible to have localized ultra-purification facilities than to transport large quantities of this dialysate to centers. In fact, water treatment is a major expense of the dialysis treatment centers and the cost of building the treatment facility is one of the major capital expenses of building a new dialysis center. With approximately 6,500 dialysis treatment facilities in the United States, this is a major concern that needs to be addressed (see Jha, V., Chronic kidney disease: global dimension and perspectives, The Lancet, 2013, 382(9888), 260-272). These facilities consume over 170 million liters of ultra-purified water per week. Reducing water usage would reduce cost of treatments, especially in areas where water is scarce or unavailable (see Layman-Amato, R., Curtis, J., Payne, G. M., Water treatment for hemodialysis: an update, Nephrology Nursing J., 2013, 40(5), 383-404, 465. Unfortunately, because copious amounts of water are needed in each dialysis treatment (120-140 L/patient/treatment, 3 times weekly) when water is unavailable and impure, for example in Houston after Hurricane Harvey, the source unavailability will ultimately lead to patient mortality.

DESCRIPTION OF RELATED ART

Efforts in this area include those described in U.S. Pat. Nos. 5,507,723, 7,326,576, 9,215,985, 9,267,845, and 9,550,020. Although the aforementioned publications have provided methods to monitor or optimize dialysis progress, there remains a need for systems and methods that reduce the water waste associated with the procedure.

SUMMARY OF THE INVENTION

The present inventors have designed a system to continuously monitor, in real-time, the small molecules being dialyzed during hemodialysis treatment using Raman spectroscopy and press control algorithms. By monitoring the treatment, the goal is to dramatically reduce the amount of water needed per dialysis treatment by optimizing saturation of one or more analyte(s) in the dialysate and optimizing removal of wastes. This will significantly conserve water and reduce the cost of dialysis treatments, possibly reducing the amount of time necessary for dialysis treatment, improving quality of life for patients during and after treatment, and reducing the costs of building new treatment centers as well as operating costs.

Embodiments include Aspect 1, which is a dialysis system comprising: a base unit capable of performing dialysis treatment; a Raman spectrometer operably coupled to a dialysate waste line of the base unit; and a flow control unit in communication with a dialysate pump of the base unit for regulating flow of a dialysate; wherein the flow control unit is configured to receive from the Raman spectrometer one or more Raman spectrum of at least a portion of the dialysate, process one or more of the Raman spectrum, determine the concentration of one or more analytes in the dialysate, and deliver a signal to the dialysate pump, modulating the flow of the dialysate.

Such embodiments can include Aspect 2, which is the system of Aspect 1, wherein the base unit comprises at least: one or more dialysate pump; one or more dialysis filter; one or more dialysate input line for providing fresh dialysate to the filter; one or more dialysate waste line for carrying used dialysate to waste.

Aspect 3 is the system of Aspect 1 or 2, further comprising a sampling chamber connected to the dialysate waste line.

Aspect 4 is the system of any of Aspects 1-3, further comprising one or more solenoid(s) for diverting dialysate flow for sample collection.

Aspect 5 is the system of any of Aspects 1-4, wherein the flow control unit is a proportional-integral-derivative controller.

Aspect 6 is the system of any of Aspects 1-5, wherein the flow control unit contains a Raspberry Pi microprocessor.

Aspect 7 is the system of any of Aspects 1-6, wherein the dialysate pump is a step-motor based peristaltic pump.

Aspect 8 is the system of any of Aspects 1-7, wherein the signal delivered to the dialysate pump is a variable frequency, constant duty cycle pulse width modulated signal.

Aspect 9 is the system of any of Aspects 1-8, further comprising one or more solenoid(s) and/or solid-state relays to divert at least a portion of the dialysate flow to a sampling chamber for data collection.

Aspect 10 is the system of any of Aspects 1-9, wherein the system is configured such that the portion of the dialysate flow diverted for sample collection stops moving once inside the sampling chamber, a light emitting source of the Raman spectrometer is turned on, Raman spectra are collected, the light emitting source is turned off, and the dialysate flow resumes.

Aspect 11 is the system of any of Aspects 1-10, wherein one or more of the analyte(s) are chosen from urea, creatinine, or both.

Aspect 12 is the system of any of Aspects 1-11, wherein the flow control unit is programmed to terminate dialysis treatment when analyte concentration in blood is reduced by at least 20%, by at least 30%, by at least 40%, by at least 50%, by at least 60%, by at least 70%, by at least 80%, by at least 90%, and so on, or any range in between these targeted end points, as calculated by one or more mass transfer model.

Aspect 13 is the system of any of Aspects 1-12, wherein the flow control unit is programmed to measure analyte peak from Raman spectrum, plug peak measurement into the mass transfer model, determine the new flow rate, and/or update the flow rate based on one or more mass transfer model.

Aspect 14 is the system of any of Aspects 1-13, further comprising a user interface.

Aspect 15 is a method for performing dialysis treatment comprising: providing one or more Raman spectrum of a dialysate sample during a dialysis treatment; determining a concentration of one or more analytes present in the dialysate sample; modulating dialysate flow rate in a manner that provides an amount of one or more of the analytes within a specified range.

Aspect 16 is the method of any of Aspects 1-15, wherein one or more of the analyte(s) are chosen from urea, creatinine, or both.

Aspect 17 is the method of any of Aspects 1-16, wherein the flow rate is modulated by keeping mass transfer rate constant.

Aspect 18 is a device for modulating dialysate flow rate, the device comprising: a Raman spectrometer in operable communication with a dialysate waste line of a dialysis system; a dialysate pump for moving a dialysate through the dialysate system; and a flow control unit in operable communication with the dialysate pump for modulating flow rate of a flow of a dialysate through the dialysis system; wherein the flow control unit is configured to: (i) receive from the Raman spectrometer one or more Raman spectrum of the dialysate exiting a dialysis filter of the dialysis system, (ii) process the Raman spectrum, (iii) determine a concentration of one or more analytes in the dialysate exiting the dialysis filter of the dialysis system, and (iv) deliver a signal to the dialysate pump, to modulate the dialysate flow rate.

Aspect 19 is the device of any of Aspects 1-18, further comprising a sampling chamber and one or more solenoids and/or solid-state relays to divert the dialysate flow to the sampling chamber.

Aspect 20 is the device of any of Aspects 1-19, further comprising data storage for gathering patient profiles.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

DETAILED DESCRIPTION OF VARIOUS EMBODIMENTS OF THE INVENTION

Figure 1:
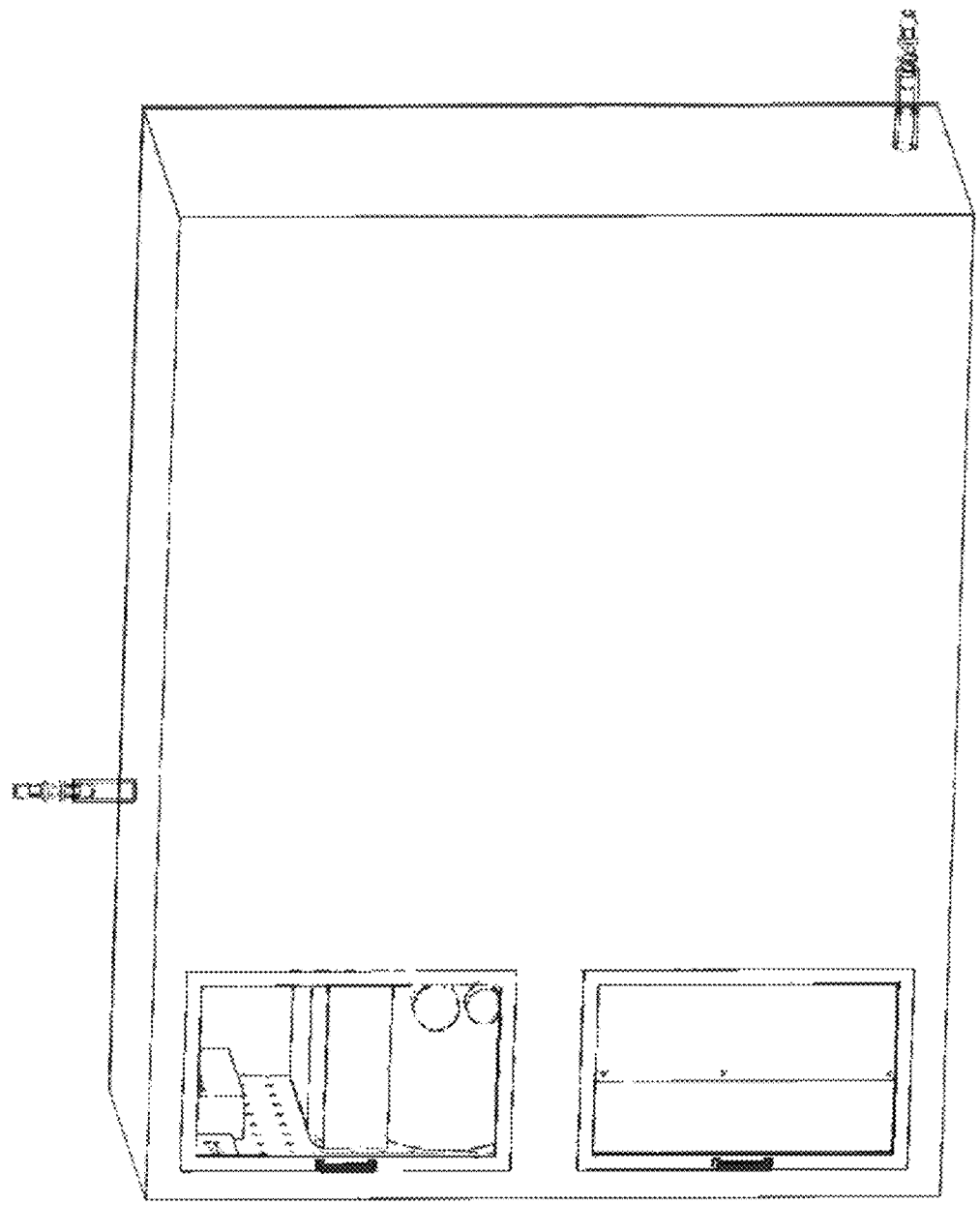
FIG. 1 is a schematic diagram that depicts a representative device designed to control dialysis flow rate according to embodiments of the invention.
Figure 2:
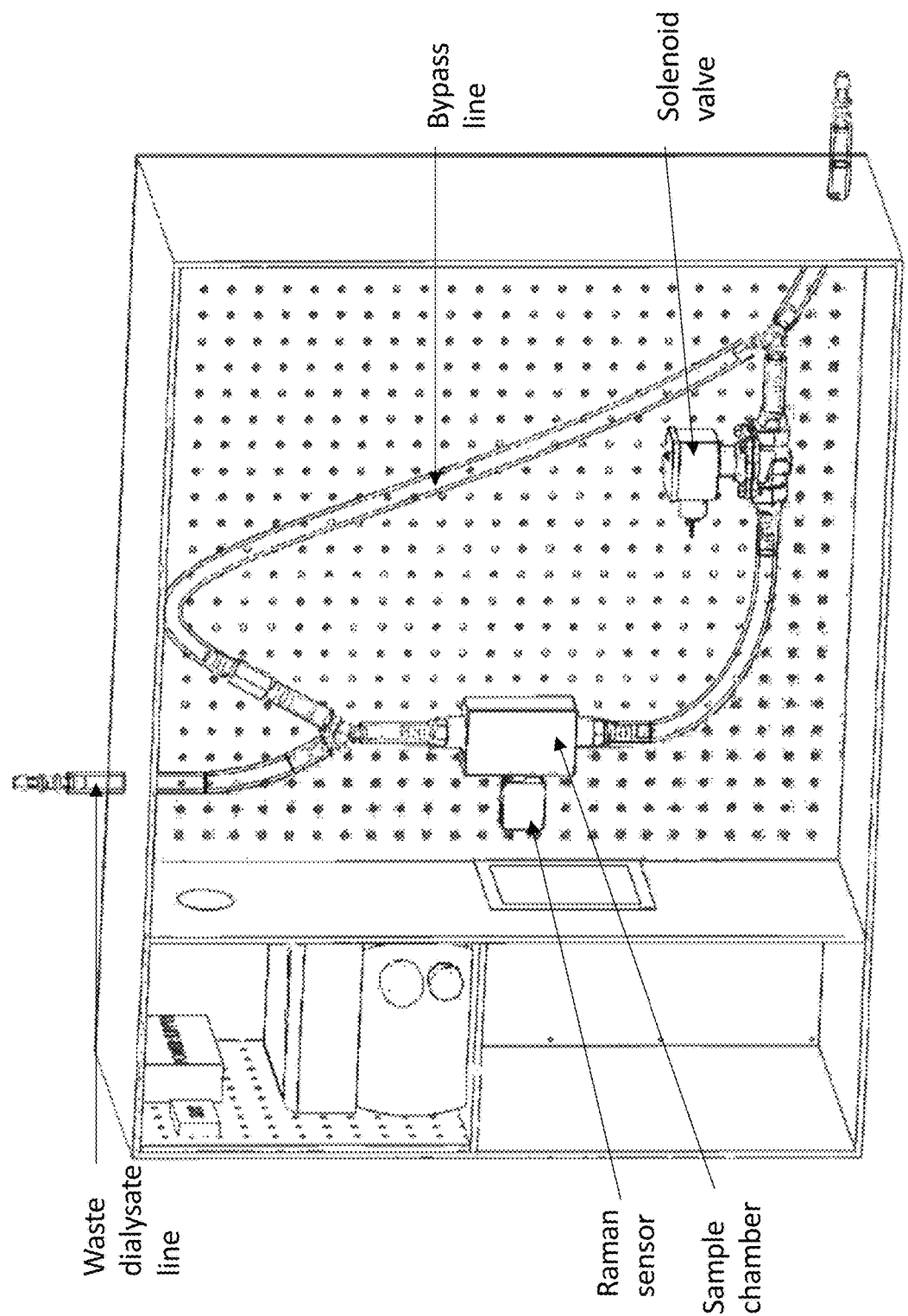
FIG. 2 is a schematic diagram that depicts representative internal components of the device shown in FIG. 1.
Figure 3B:
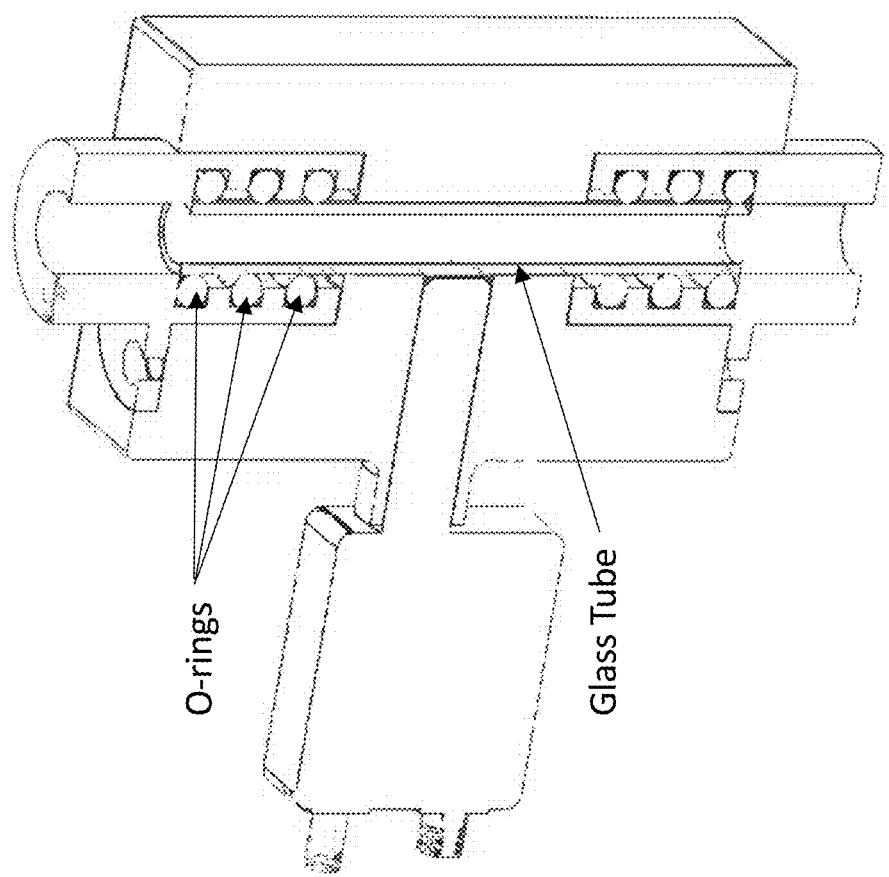
FIG. 3B is a schematic diagram showing a cross section of the sampling chamber shown in FIG. 3A.
Figure 3A:
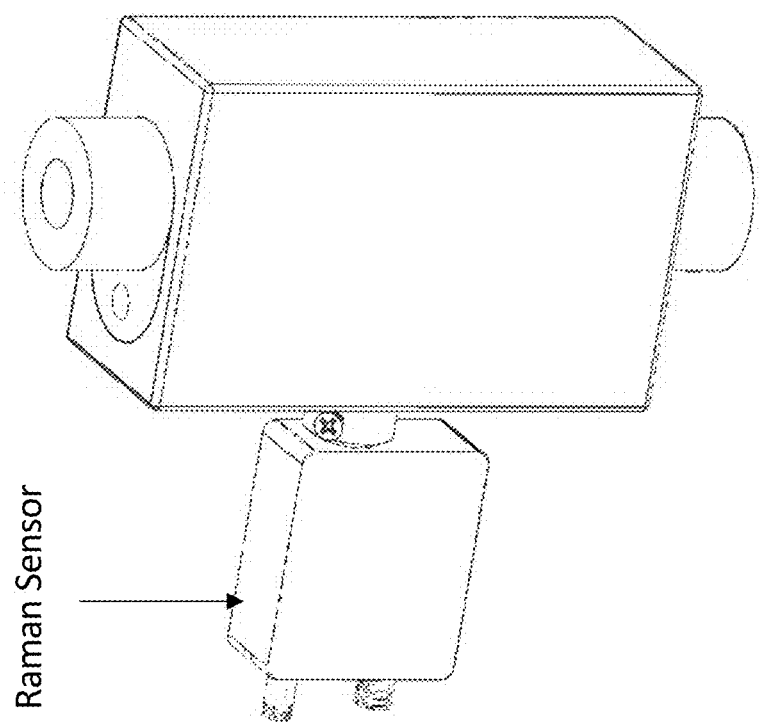
FIG. 3A is a schematic diagram that depicts a representative sampling chamber of the device of FIG. 1.
Figure 4D:
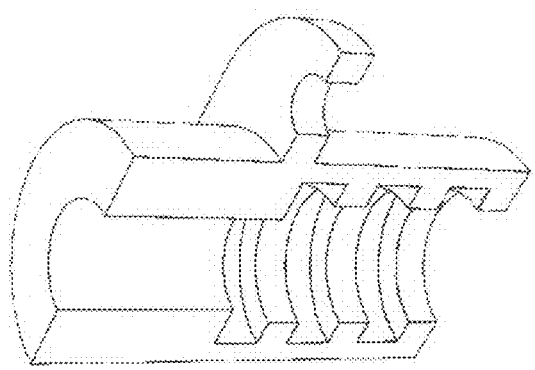
FIG. 4D is a schematic diagram showing a component of the sampling chamber shown in FIG. 3A.
Figure 4C:
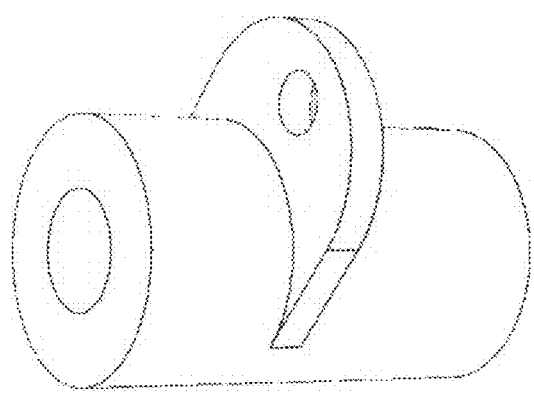
FIG. 4C is a schematic diagram showing a component of the sampling chamber shown in FIG. 3A.
Figure 4B:
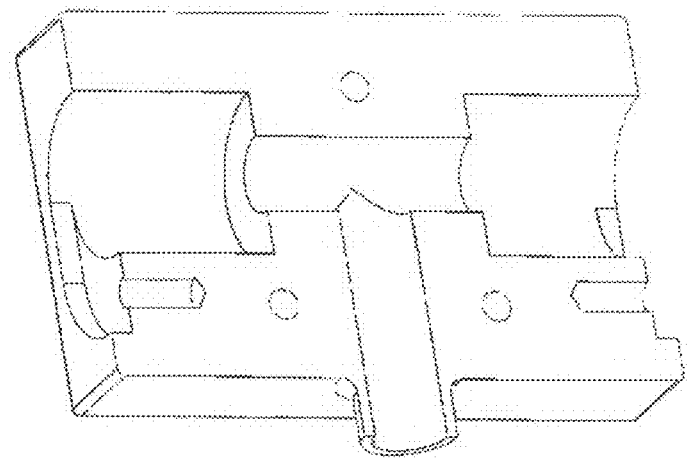
FIG. 4B is a schematic diagram showing a component of the sampling chamber shown in FIG. 3A.
Figure 4A:
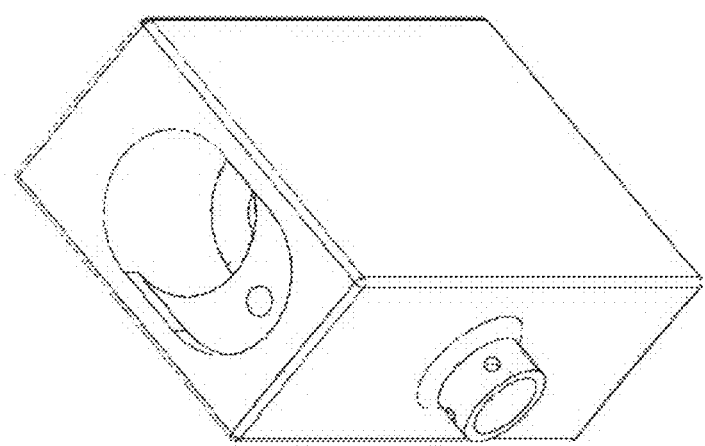
FIG. 4A is a schematic diagram showing a component of the sampling chamber shown in FIG. 3A.
Figure 5:
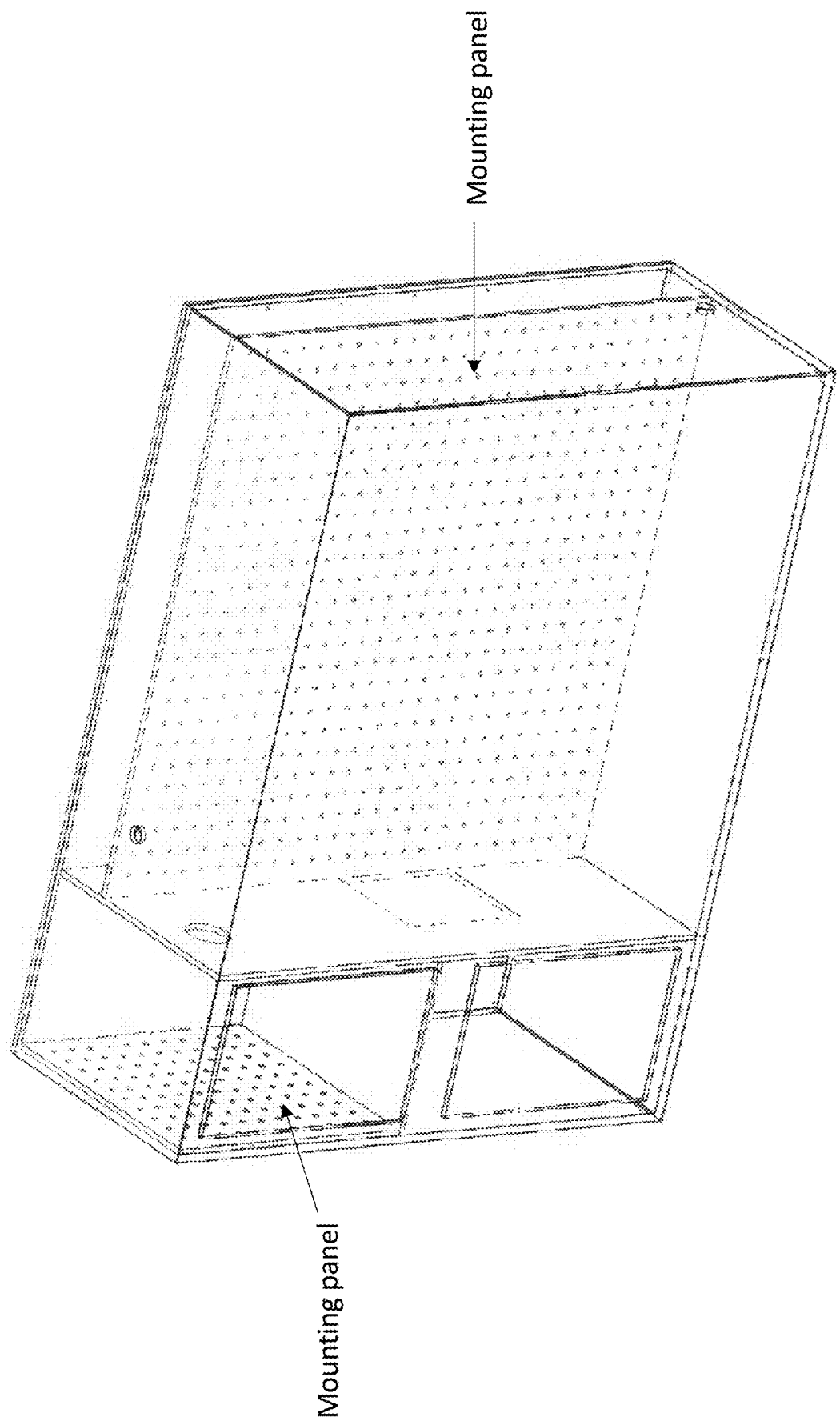
FIG. 5 is a schematic diagram that depicts a representative enclosure for the device shown in FIG. 1.

The Smart Hemodialysis Device (SHD) can individualize hemodialysis treatment by using energized radiation to analyze the concentration of impurities in a patient's waste dialysate. Using this data, the flow rate of dialysate can be adjusted in order to optimize treatment and conserve dialysate. The company DialySensors has developed a fluid controls system (FIGS. 1-5), mass transfer model, and calibration process to work in conjunction with a method of energized radiation. The SHD can intake waste dialysate, collect sample data periodically, and automatically adjust the flow rate of dialysate accordingly in real time. Furthermore, the device can create a patient profile in which historical data can be recorded that will help doctors better understand patients' responses to various levels of hemodialysis treatment.

Hemodialysis is the most popular treatment for patients with chronic or severe kidney diseases. Despite their specific diagnosis or condition, every patient is subjected to the same flow rate of dialysate through the dialyzer. Clearance goals are based on blood concentrations sampled on a monthly basis. Barely any information is gathered from patients during treatment to monitor how they are responding to the treatment. By monitoring the chemical composition of the waste dialysate throughout treatment, the patient's condition can be monitored in real time. Doctors will be able to see exactly how the patient's body responds to differing treatment settings, allowing them to personalize treatment for each individual patient. Receiving individual care by adjusting the flow rate of dialysate will lessen the volume of dialysate used, shorten treatment times, and improve patient outcome and quality of life.

Monitoring the chemical composition of the waste dialysate in real time will allow the device to gather patient profiles. The profiles will operate in accordance with HIPPA guidelines in order to protect patients' privacy. Patient profiles will allow for detailed, real-time medical studies to be conducted on the hemodialysis treatment. Doctors will have real-time treatment data at their fingertips to analyze and provide the best treatment options for their patients.

Individualizing treatment by measuring the amount of waste left in each patient could result in a shorter treatment time. By this process of individualizing treatment and lowering dialysate flow rates, the SHD will reduce the amount of dialysate used in hemodialysis. Previous research shows that lowering the flow rate of dialysate over the duration of a dialysis treatment results in the same amount of waste being removed from a patient compared to constant flow rate. Reduced flow rate of dialysate over the course of a treatment of the same duration results in a reduction in the dialysate used.

By continuously monitoring the molecular diffusion across the dialyzer membrane with Raman spectroscopy, Proportional Integral Derivative (PID) controls for example can be used to adjust the flow rate of dialysate depending on molecular concentrations in patients' blood. By continuously monitoring molecules, like urea and/or creatinine, in the blood during dialysis, the flow rate of the dialysate can be adjusted/controlled to keep concentrations of molecules in the waste line within a specified range, such as at a consistent target level. As the concentration of urea or other analyte(s) reaches steady state, the flow rate of dialysate can be reduced from the 675 mL/min constant speed of current treatments to a lower rate while maintaining urea/analyte extraction. By reducing the amount of dialysate used per treatment, the system and methods can significantly reduce the amount of ultrapure water needed for dialysis treatments for the 465,000 individuals in the United States that require dialysis on a recurring basis (Jha, 2013). The technology is also able to increase the flow rate of dialysate in order to clear increased levels of molecules in the blood, if perhaps, a patient releases a burst of urea later in their treatment. The benefit of using PID control to monitor blood contaminant concentrations is that the system will be able to continually adjust dialysate flow rate levels depending on the individual patient needs.

Before a patient treatment cycle, or each patient treatment cycle, a light-emitting laser can first be calibrated. Therefore, during patient setup and before patient dialyzing, the smart hemodialysis machine can send calibration fluid through the sampling chamber. After system calibration, sterilization fluid can be caused to flow through the chamber for preparation of waste dialysate testing.

A detailed process is outlined as follows:

(1) Staff begins patient setup and starts calibration process.

(2) A solenoid valve attached to a sterilization fluid line that can be energized to allow sterilization fluid to flow through the sampling chamber and out the waste line.

(3) Solenoid valve attached to sterilization line can be closed preventing more fluid to flow into the chamber.

(4) Solenoid valve energizes and allows calibration fluid to flow from bag located on the hemodialysis machine into the sampling chamber.

(5) Solenoid valve closes once sampling chamber is full.

(6) Data sampling system is calibrated based on calibration fluid.

(7) Second solenoid valve located after the sampling chamber can be energized resulting in calibration fluid to flow from sampling chamber to waste line.

(8) An indicator can be displayed on a display screen or other user interface notifying the staff when calibration is done.

Fluid Control in the Chamber

Fluid flow in the device will be controlled to allow for the collection of a sample for testing and flow adjustment. A detailed process is outlined as follows:

(1) Waste dialysate will flow into an inlet in the SHD.

(2) During device operation, the fluid will flow through a sampling chamber and out of the device, directly into a waste container.

(3) Periodically, a solenoid valve below the sampling chamber will be actuated for sample collection in which the fluid will accumulate in the chamber.

(4) Using energized radiation, the concentration of molecules in the waste dialysate will be collected and recorded.

(5) During this time, waste dialysate that is not in the sample will flow out of the device through a bypass line.

(6) Once the sample has been collected, the valve below the chamber will open and the device will resume operating as outlined in step 2.

Testing Using Energized Radiation

When it is time to take a reading of the fluid composition, the sampling procedure will take place. Fluid will stop moving through the sampling chamber so an accurate sample can be gathered. A light emitting source will energize molecules within the sample, analyzing the chemical composition of the fluid. Once sufficient readings have taken place, the light emitting source will turn off and flow will resume through the sampling chamber as normal.

An exemplary detailed process is outlined as follows:

(1) When triggered by a timer, the second solenoid valve located after the sampling chamber will close. The flow through the sampling chamber will stop, and a one way valve will prevent any backflow out of the chamber. The fluid flow will continue at the same flow rate around the sampling chamber through a bypass line.

(2) A light emitting source will energize molecules within the sample, analyzing the chemical composition of the fluid.

(3) Step 2 can be repeated if desired one or more or multiple times until a sufficient number of scans have been performed to ensure accuracy.

(4) The scans will analyze the concentrations of key molecules in the fluid and send that information to the server.

(5) The light emitting source will turn off, and the second solenoid valve will reopen. The fluid will begin flowing through the sampling chamber as normal.

Modeling Flow Rate Based on Concentration

Mass Flow Model

A mass transfer model of the dialyzer will be used to modulate the dialysate flow rate and create a patient treatment profile. Modeling the dialysis filter as a mass exchange similar to common heat exchanger provides equations used to calculate the concentration of waste molecules in the blood corresponding to the concentration measured in the waste dialysate. With the objective of reducing the urea concentration in the blood by 70%, the system will capture an initial concentration in the waste dialysate, use the mass exchange model to convert this value to the corresponding value in the blood, and create a patient treatment profile. The patient treatment profile will measure the treatment effectiveness at each flow rate setting. The blood flow rate prescribed by the physician, as well as the dialysate flow rate prescribed are used as the initial flow rate. Based on the initial concentration readings, the dialysate flow rate will be modulated within a prescribed range to optimize the reduction of waste concentrations, volume of dialysate used, and treatment time. Throughout the treatment, concentrations in the waste dialysate will be measured periodically using energized radiation, and the values will be used in a calibration curve to determine the next dialysate flow rate. The corresponding concentrations and flow rates will also be displayed by way of the user interface and recorded for post analysis.

Mass transfer rate (J) can be calculated as follows:

$$J = Q_{blood} * \Delta C_{blood}$$

The concentration of urea in blood can be calculated from the concentration of urea in the waste dialysate:

$$C_{blood} = \frac{C_{waste\ dialysate}}{Z} \left( \frac{1 - e^{-N_T(1-Z)}}{1 - Ze^{-N_T(1-Z)}} \right)$$

Data Collection

The system design for the Smart Hemodialysis device uses energized radiation to determine urea content in the dialysate waste and individualizes each treatment based on real time urea content. The molecular detector is integrated into an aluminum chamber with a glass tube fitting to capture and test waste fluids. The detector provides a concentration reading for urea in the waste. The urea concentration is then used in a mass balance equation, derived from the hemodialysis filter specifications, to estimate the concentration of urea in the patient's blood stream. After at least two readings, the rate of mass transfer can be estimated and the dialysate flow rate can be modulated accordingly. With a goal of 70% Urea reduction, the rate of Urea removal predicts how much flow is needed to reach the 70% goal, and flow rates can be reduced if the goal can be achieved at a lower rate. The reduction of dialysate flow per treatment reduces the total dialysate needed per center, thus saving significant money for the treatment center.

Figure 6:
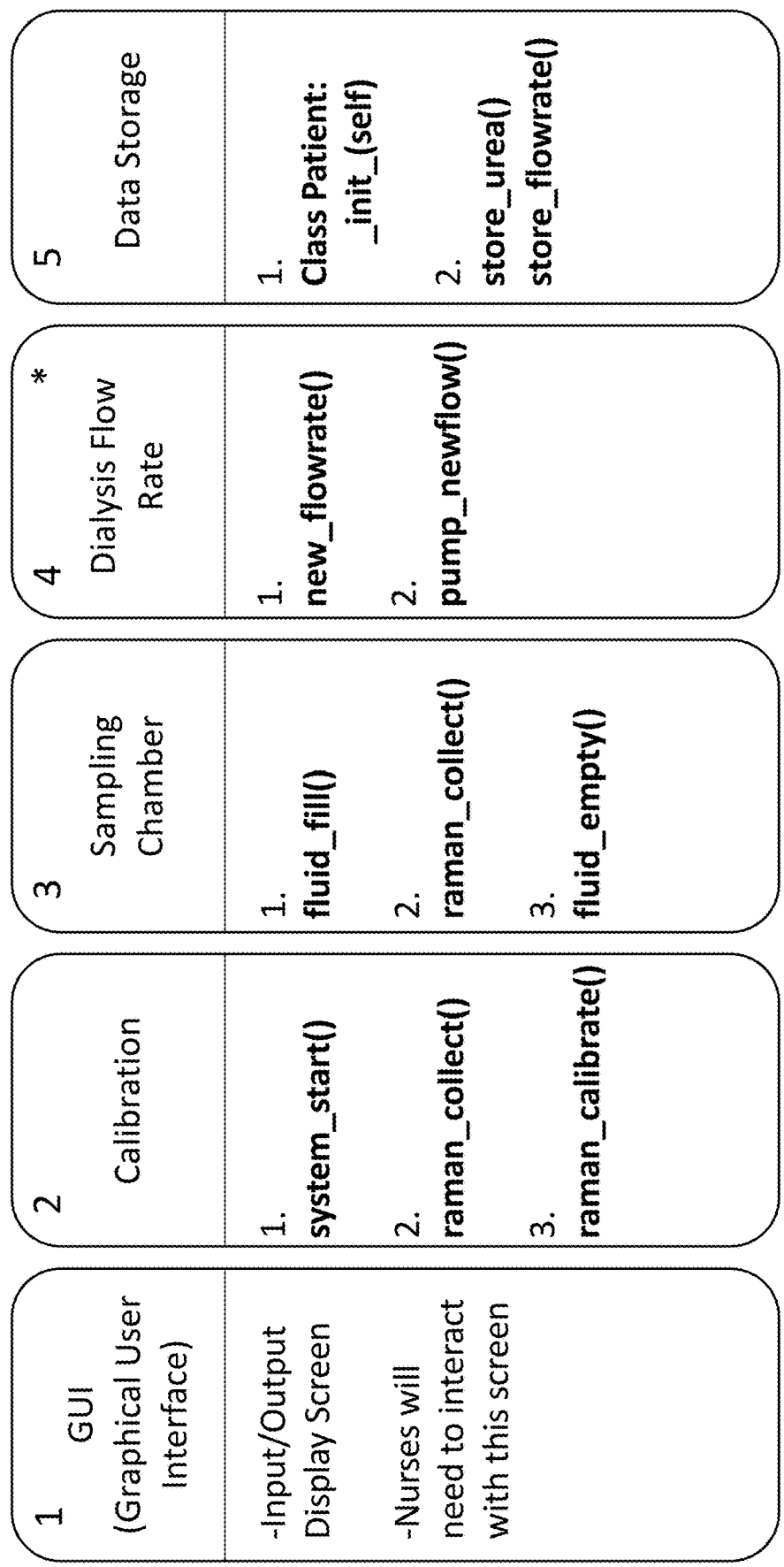
FIG. 6 is a diagram that depicts five exemplary steps involved in the Smart Hemodialysis control loop according to embodiments of the invention.
Figure 7:
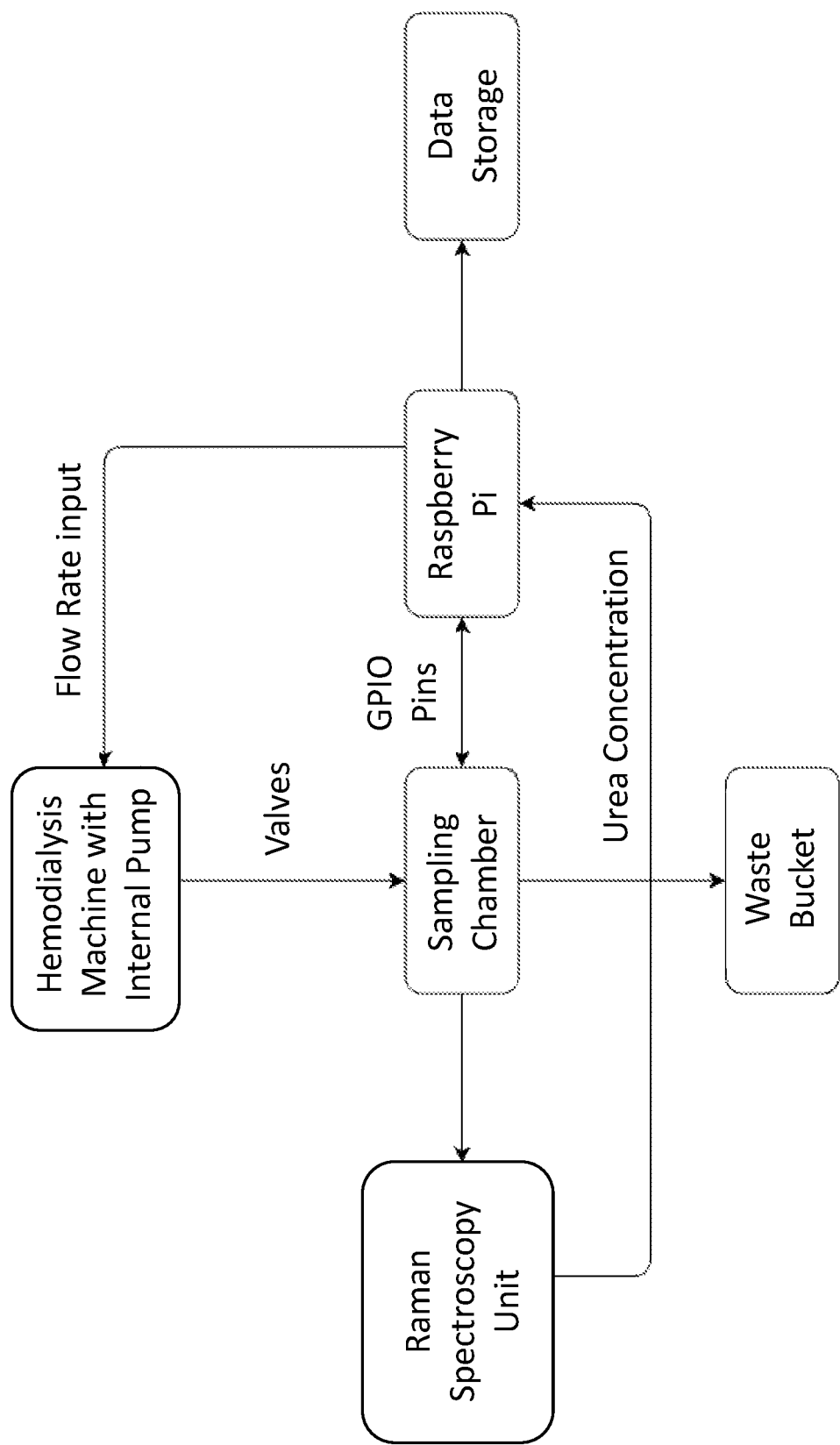
FIG. 7 is a control loop block diagram that outlines the function and communication paths used in the Smart Hemodialysis system according to embodiments of the invention.

In embodiments of the invention, the system uses a control loop with molecular concentration readings as the feedback, and a microprocessor unit to handle the calculations and communication with a dialysis system, such as the Fresenius Dialysis Machine. All gathered data is stored on a designated hard drive, server, or other data storage device(s), with local data storage device(s) being preferred to prevent the need for network security. An exemplary feedback loop for the Smart Hemodialysis system is shown in FIGS. 6 and 7.

Figure 8:
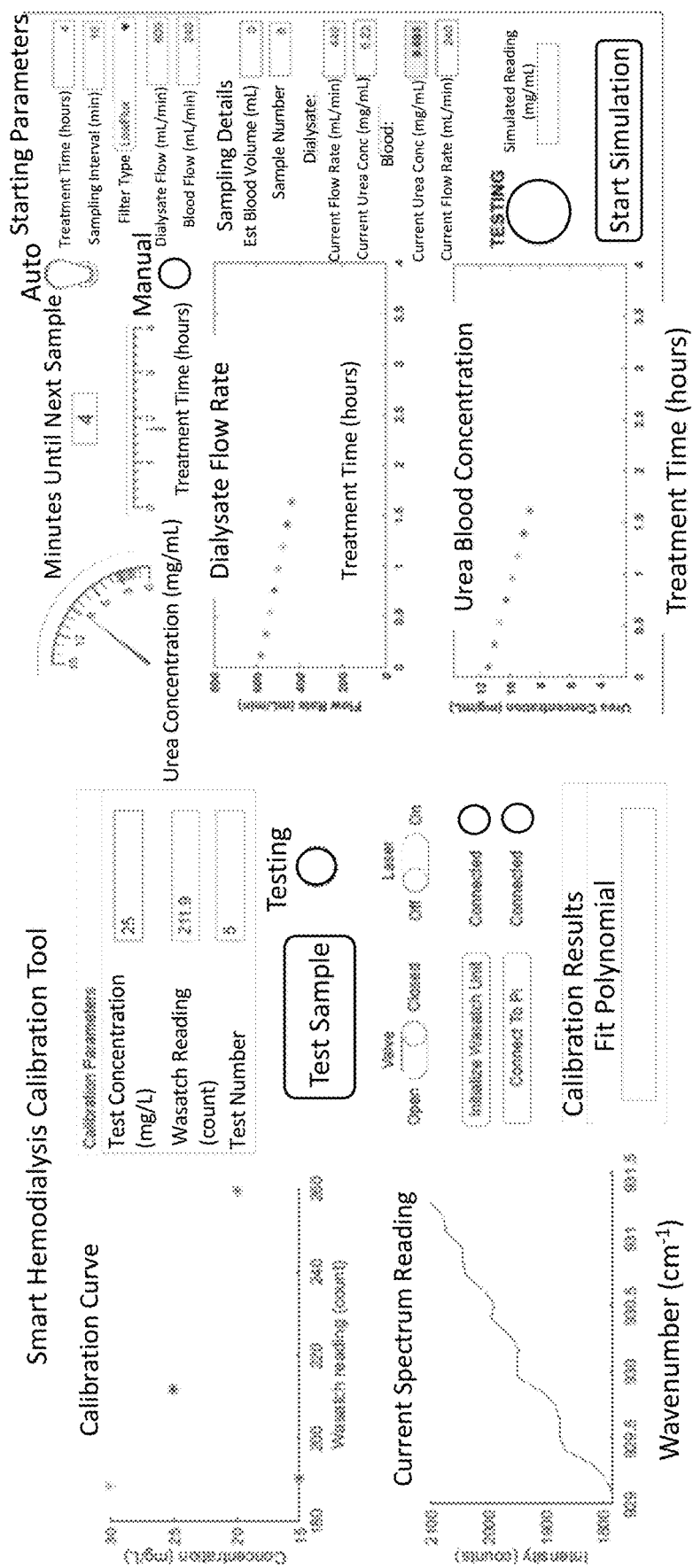
FIG. 8 is a diagram showing representative components of a user interface.
Figure 9:
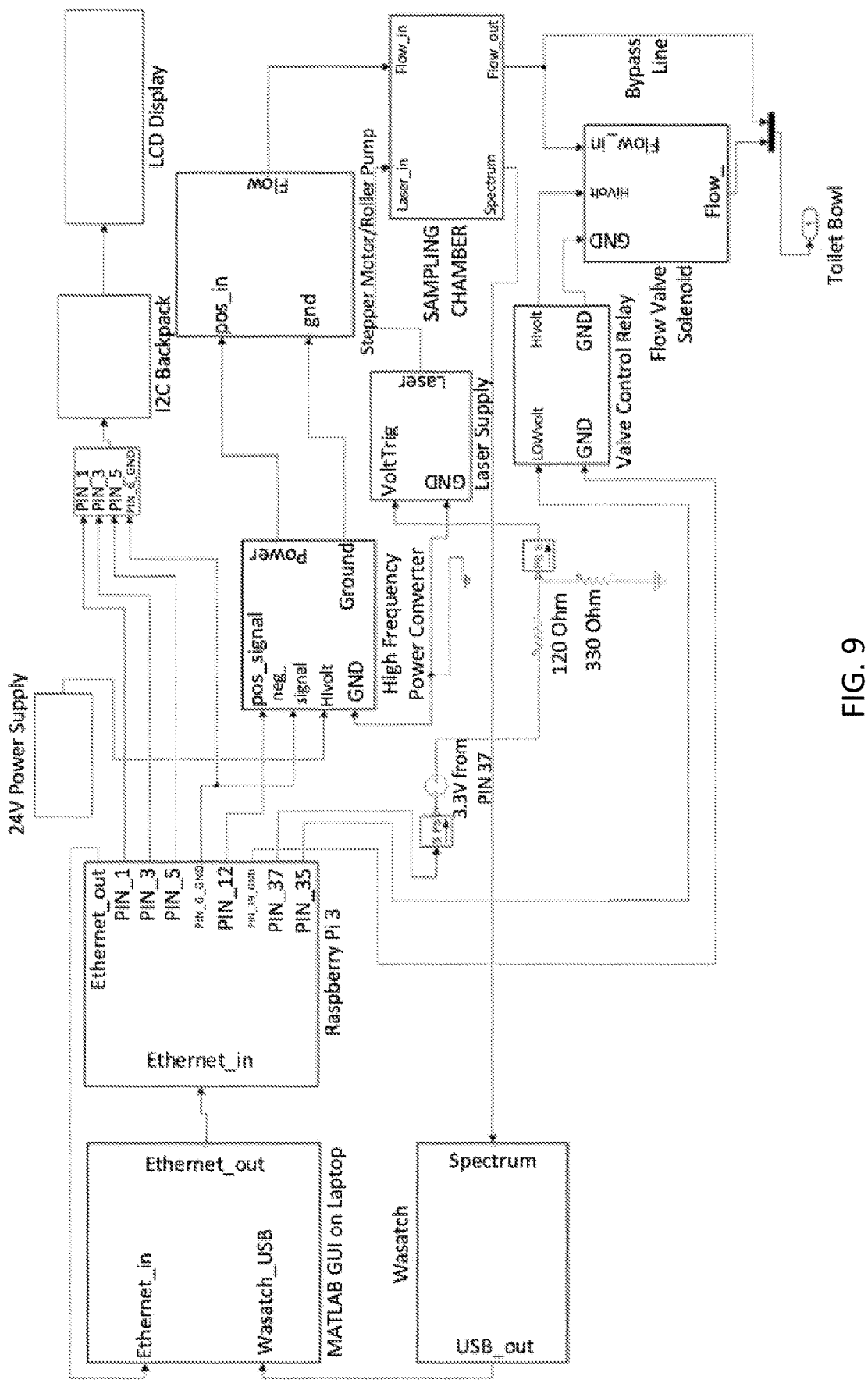
FIG. 9 is a diagram depicting various components of an exemplary Smart Hemodialysis system according to an embodiment of the invention.
Figure 10:
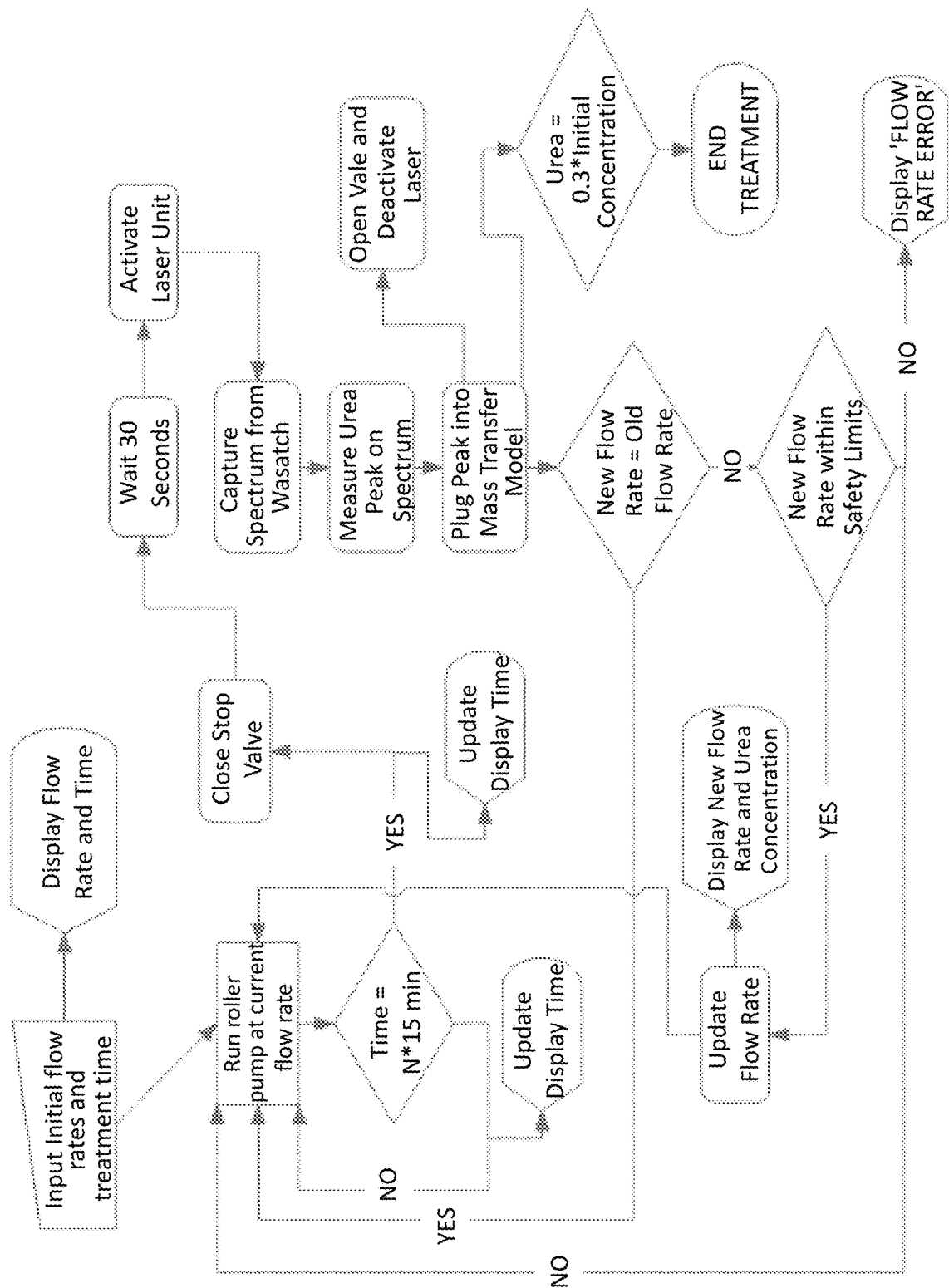
FIG. 10 is a flow chart showing an exemplary algorithm for use with the Smart Hemodialysis system according to an embodiment of the invention.
Figure 11A:
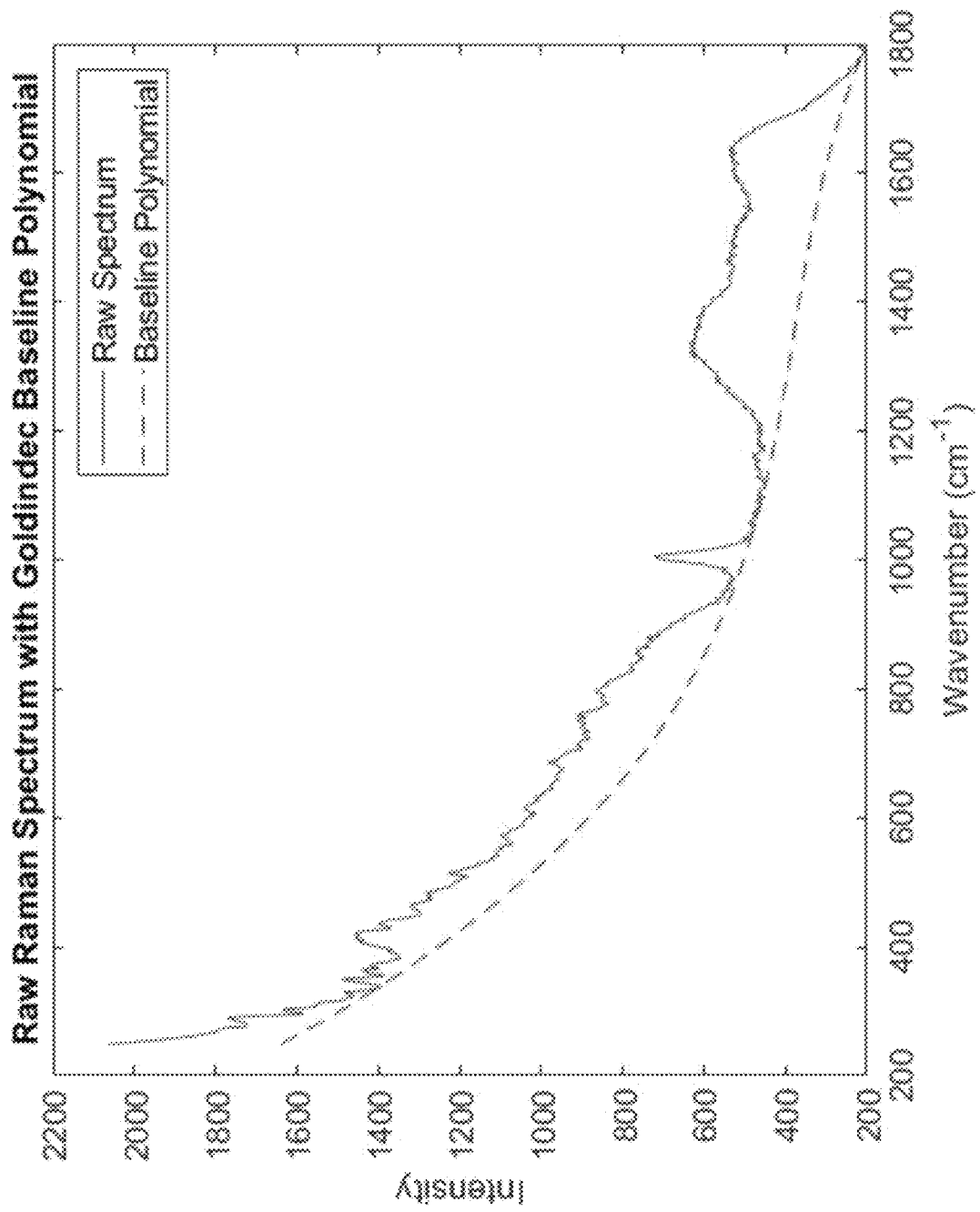
FIG. 11A is a graph depicting example raw Raman spectra with a urea peak according to an embodiment of the invention.
Figure 11B:
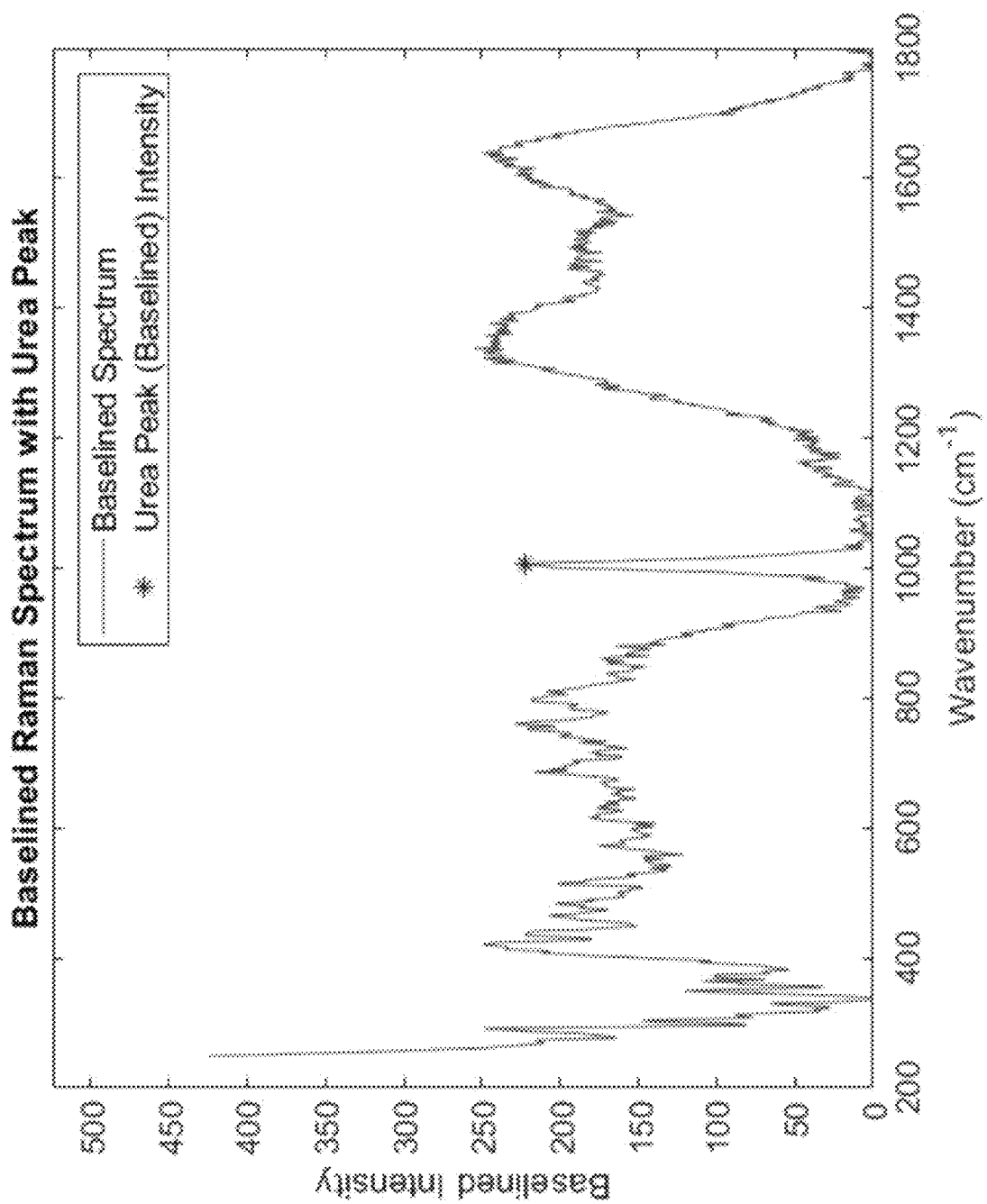
FIG. 11B is a graph depicting example Raman spectra with a urea peak according to an embodiment of the invention.
Figure 12:
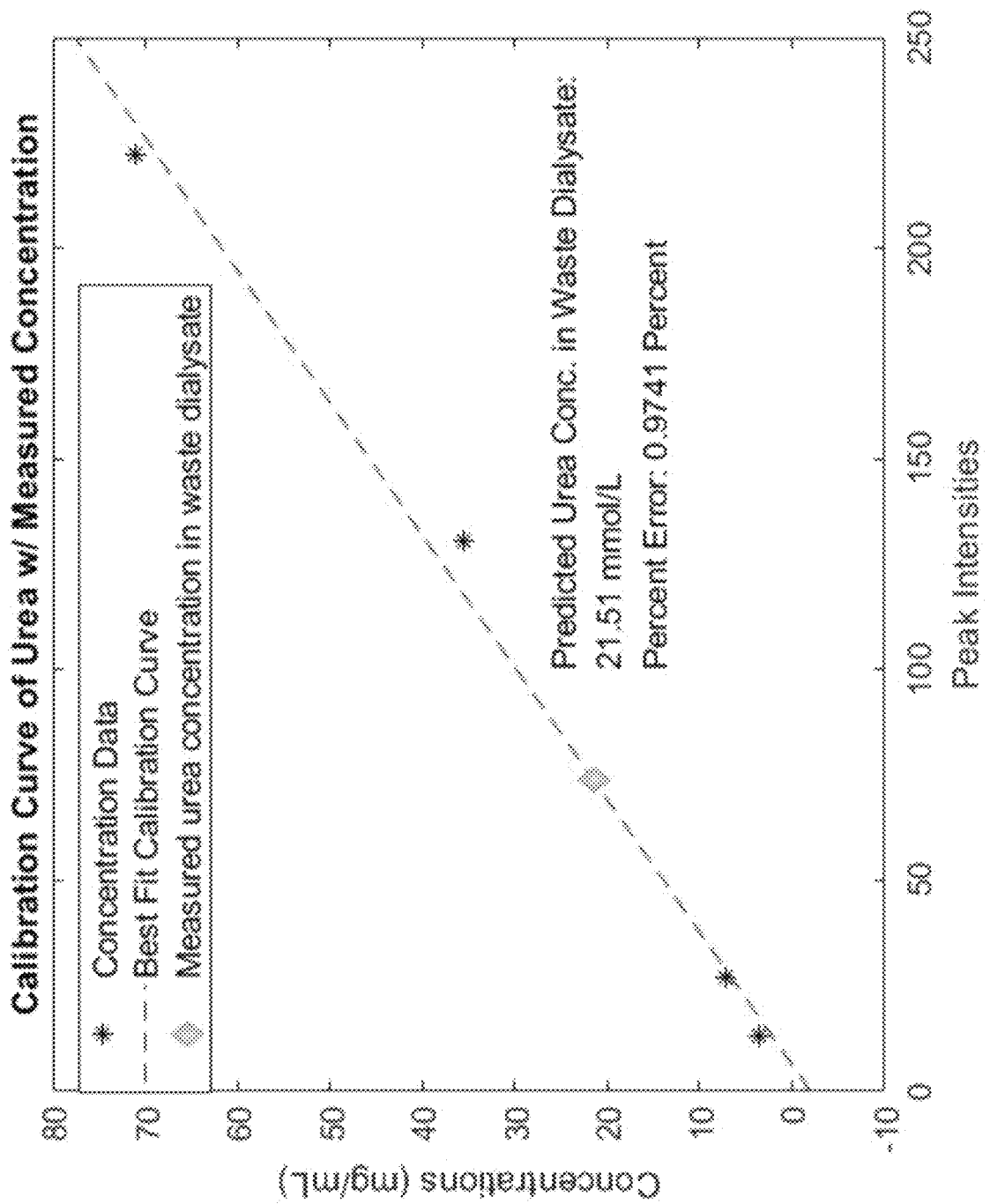
FIG. 12 is a graph depicting an example calibration curve according to an embodiment of the invention.
Figure 13:
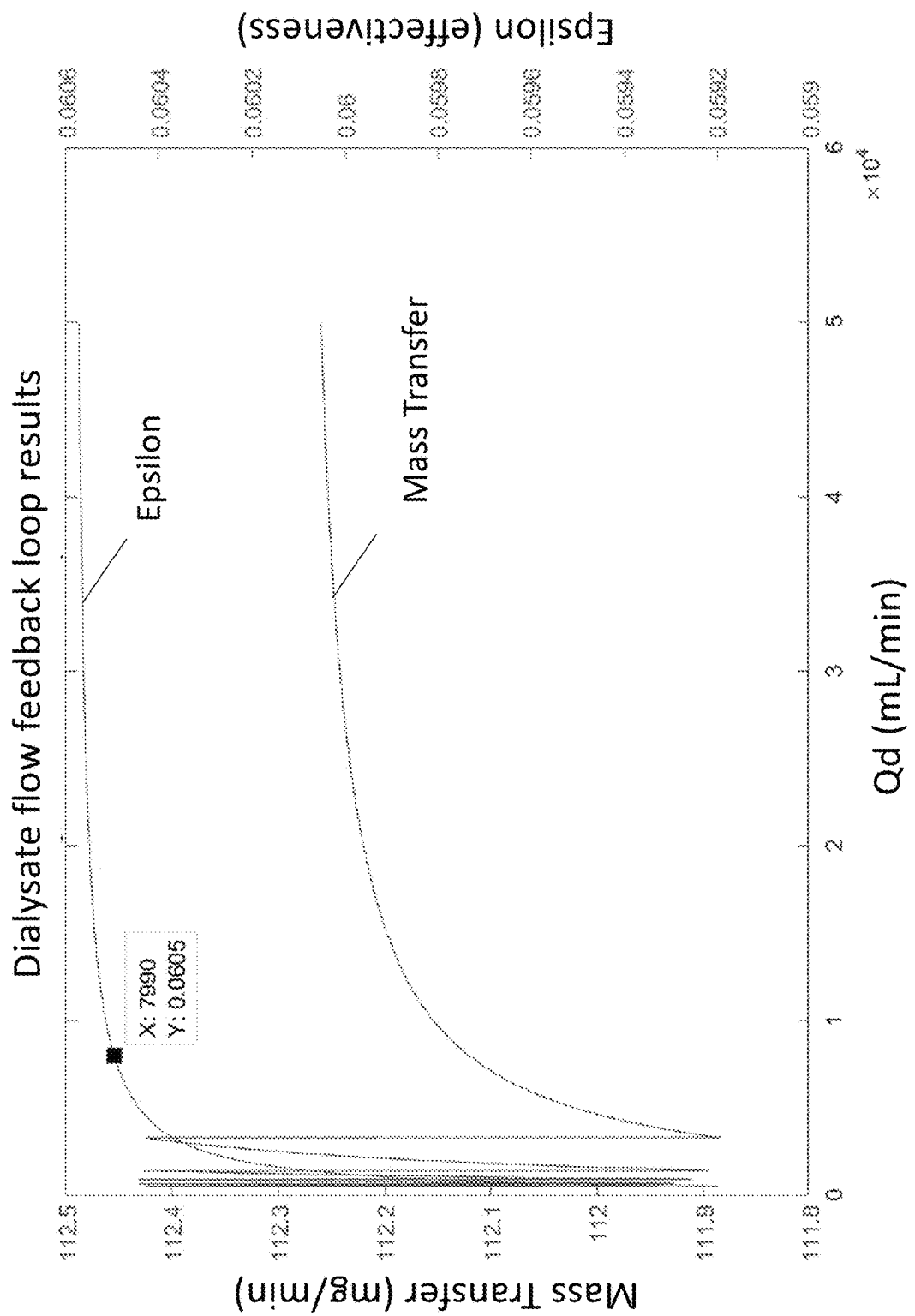
FIG. 13 is a graph showing dialysate flow feedback loop results according to an embodiment of the invention.
Figure 14:
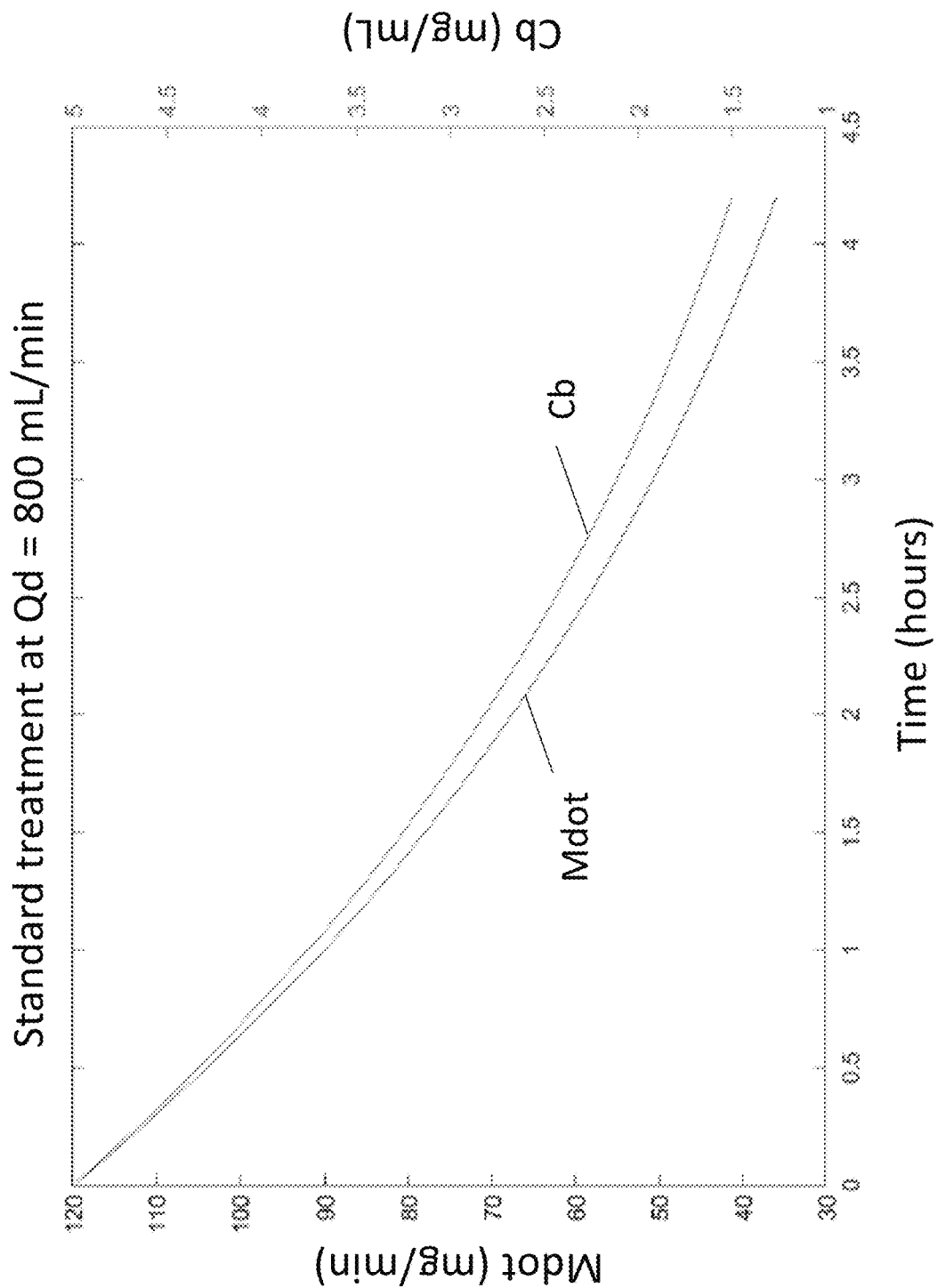
FIG. 14 is a graph of a feedback flow change model according to embodiments.
Figure 15:
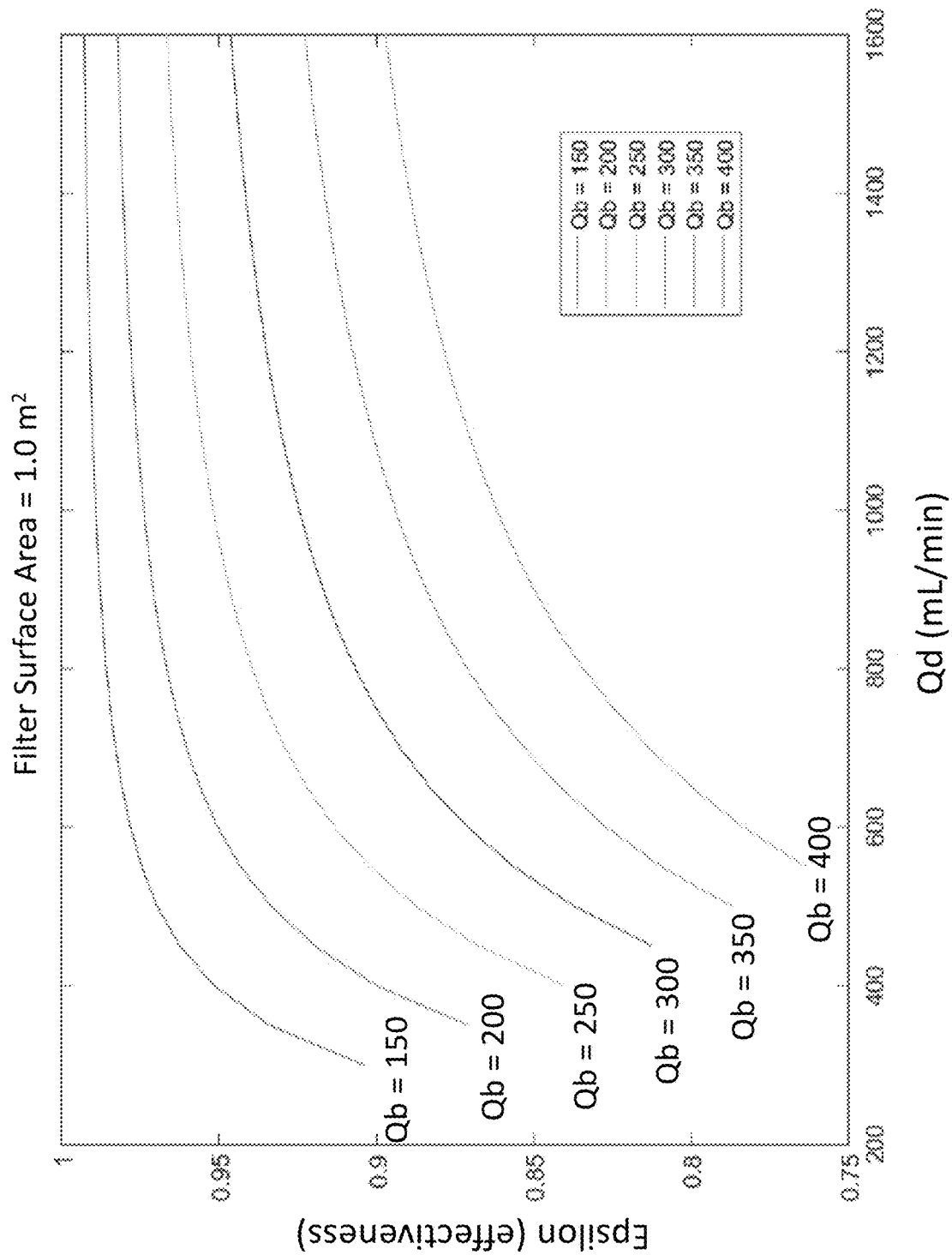
FIG. 15 is a graph showing the effectiveness of various blood flow rates (Qb) vs. dialysate flow rate (Qd) with a filter surface area of 1.0 m$^2$, according to embodiments.
Figure 16:
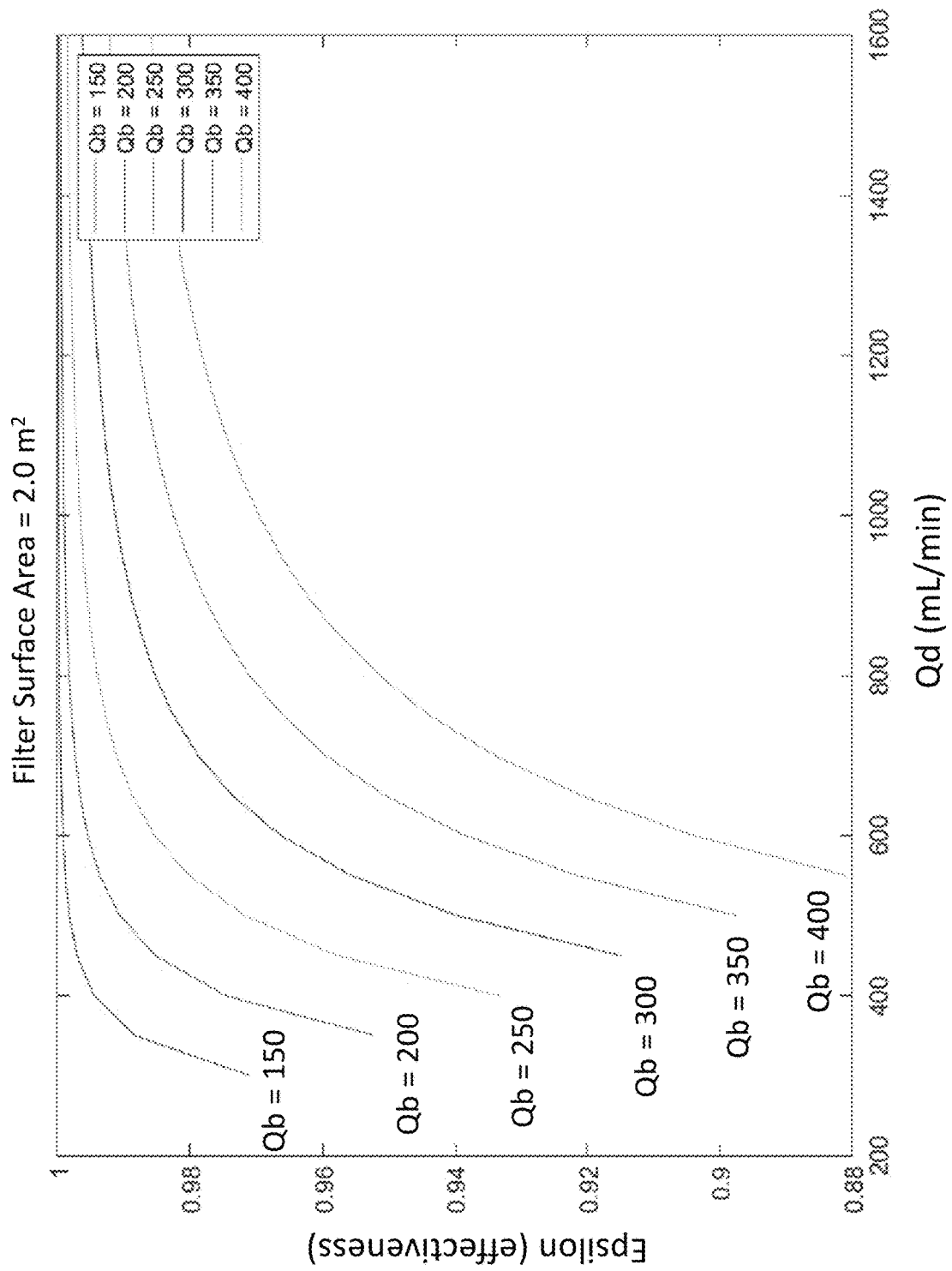
FIG. 16 is a graph showing the effectiveness of various blood flow rates (Qb) vs. dialysate flow rate (Qd) with a filter surface area of 2.0 m$^2$, according to embodiments.
Figure 17:
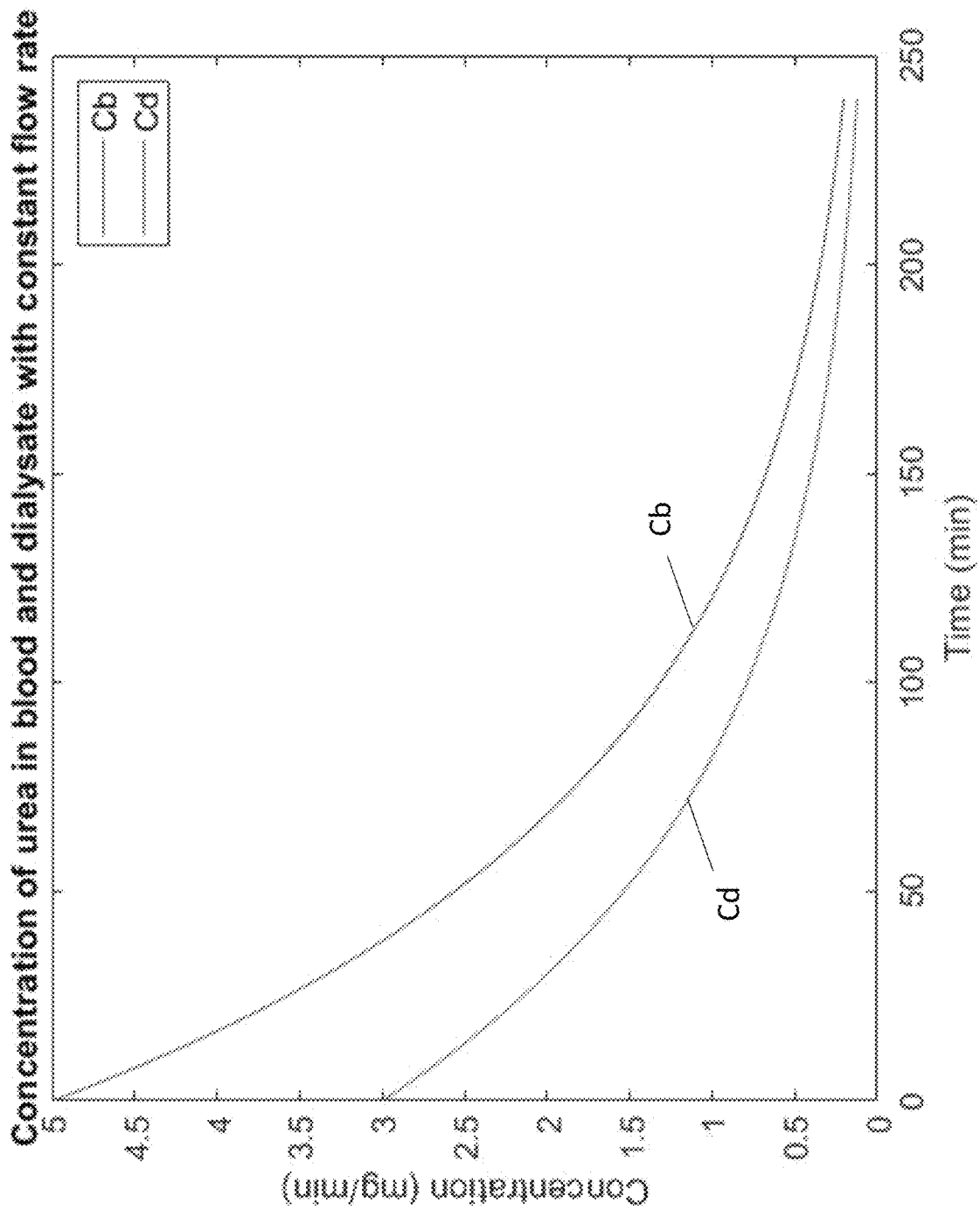
FIG. 17 is a graph showing the concentration of urea in blood and dialysate with a constant flow of dialysate.
Figure 18A:
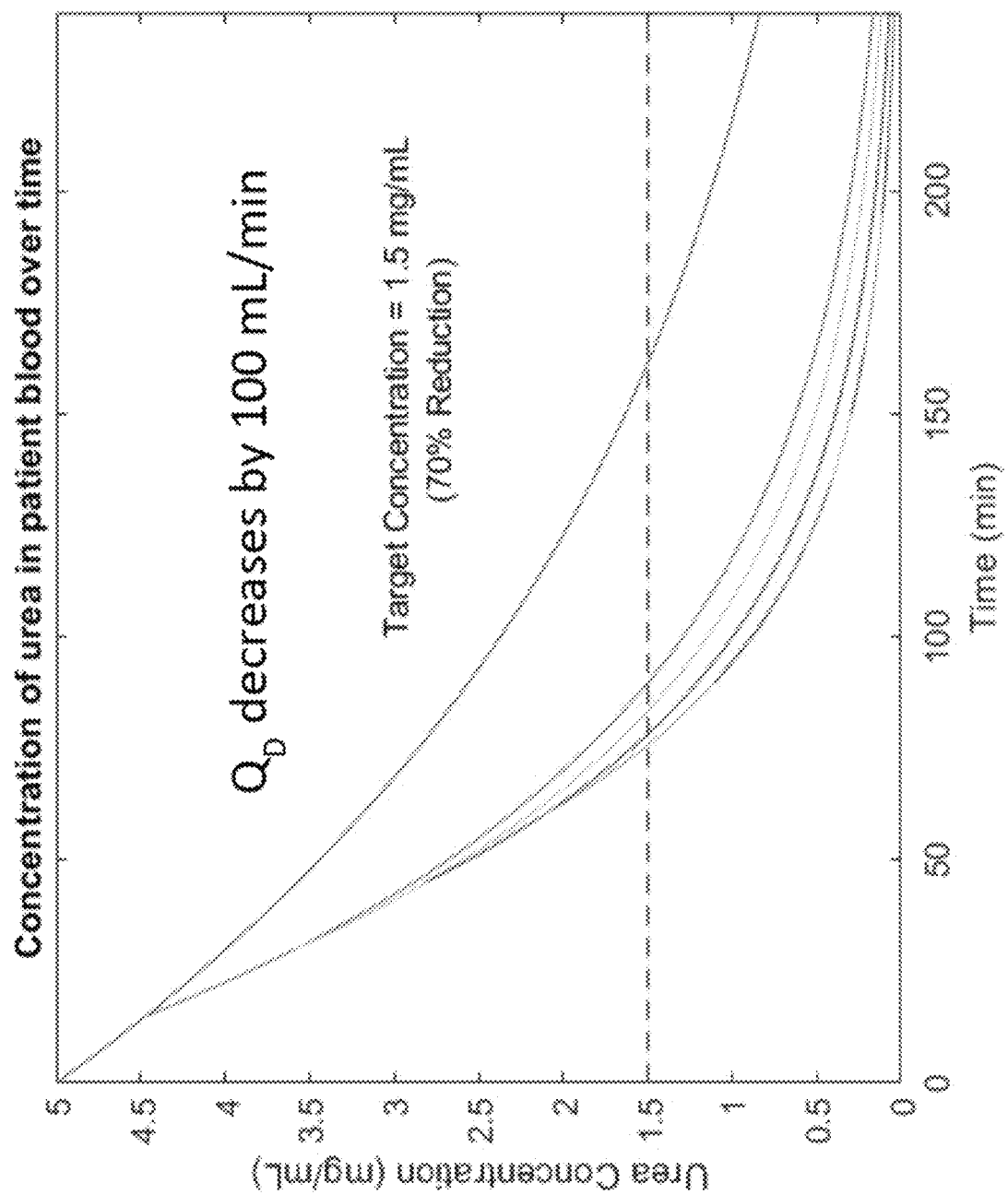
FIG. 18A is a graph depicting the concentration of urea in patient blood over time with a $Q_D$ degrease of 100 mL/min, according to an embodiment of the invention.
Figure 18B:
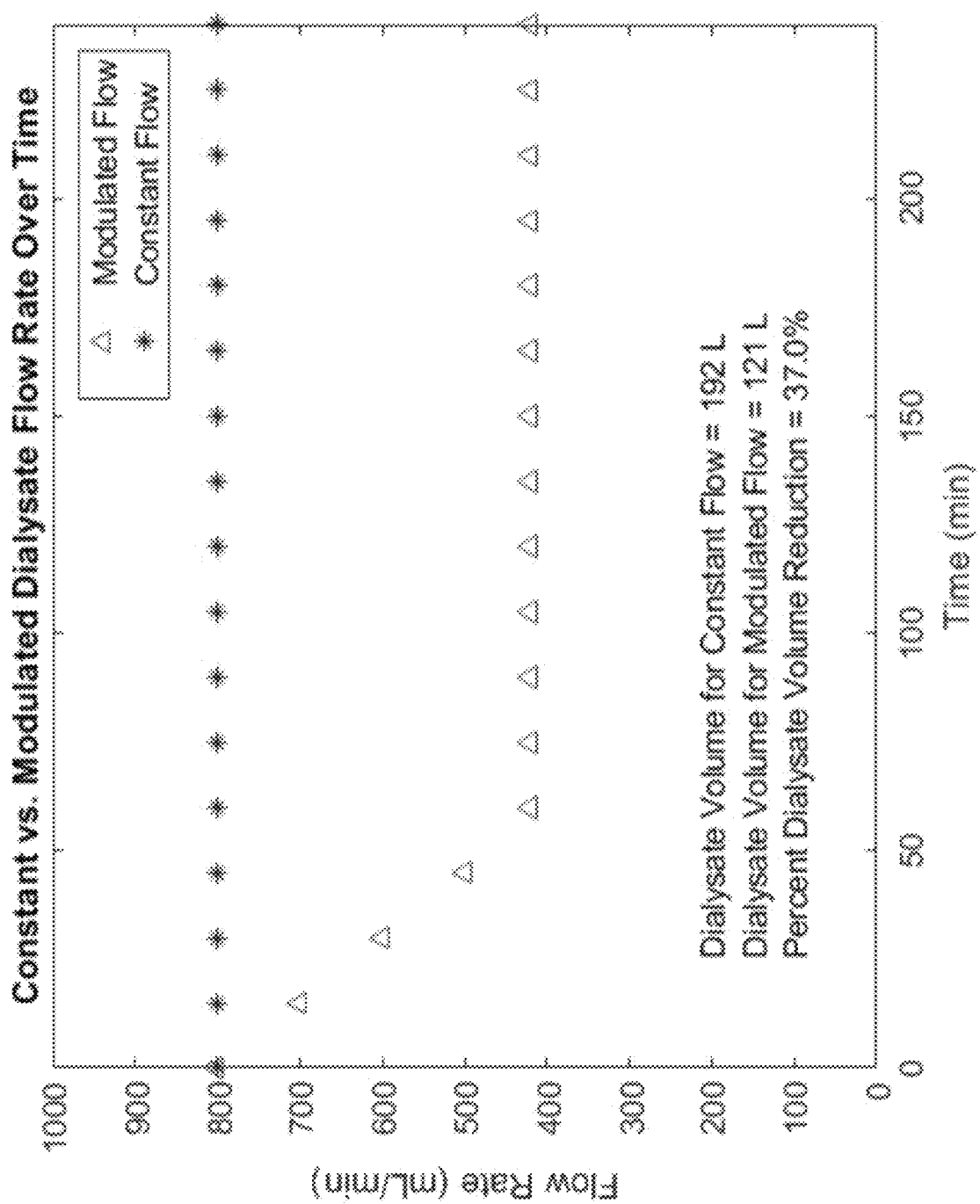
FIG. 18B is a graph comparing the flow rates of a constant flow system vs. a modulated flow system with a $Q_D$ decrease of 100 mL/min, according to embodiments.
Figure 19A:
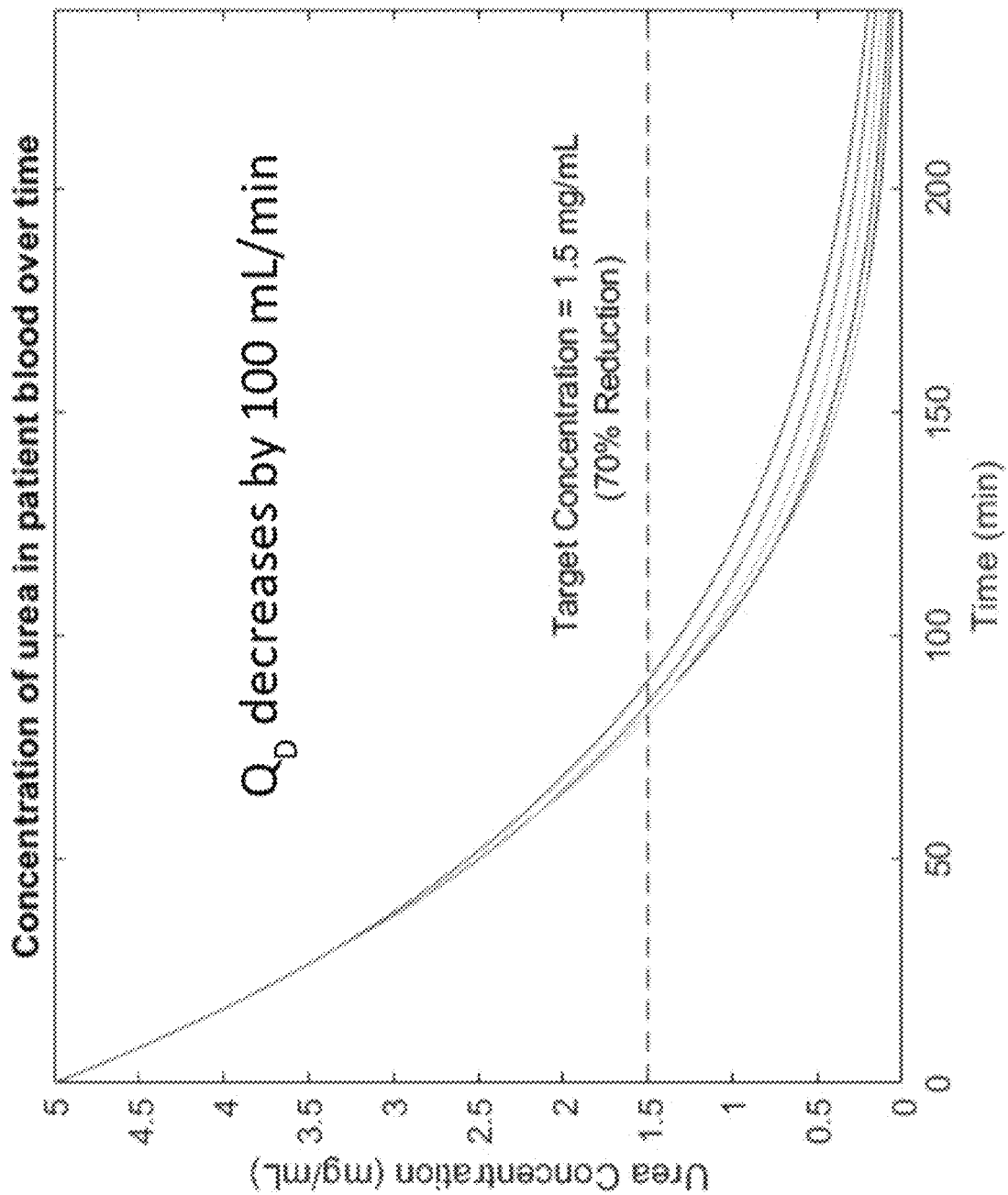
FIG. 19A is a graph depicting the concentration of urea in patient blood over time with a $Q_D$ degrease of 100 mL/min, according to an embodiment of the invention.
Figure 19B:
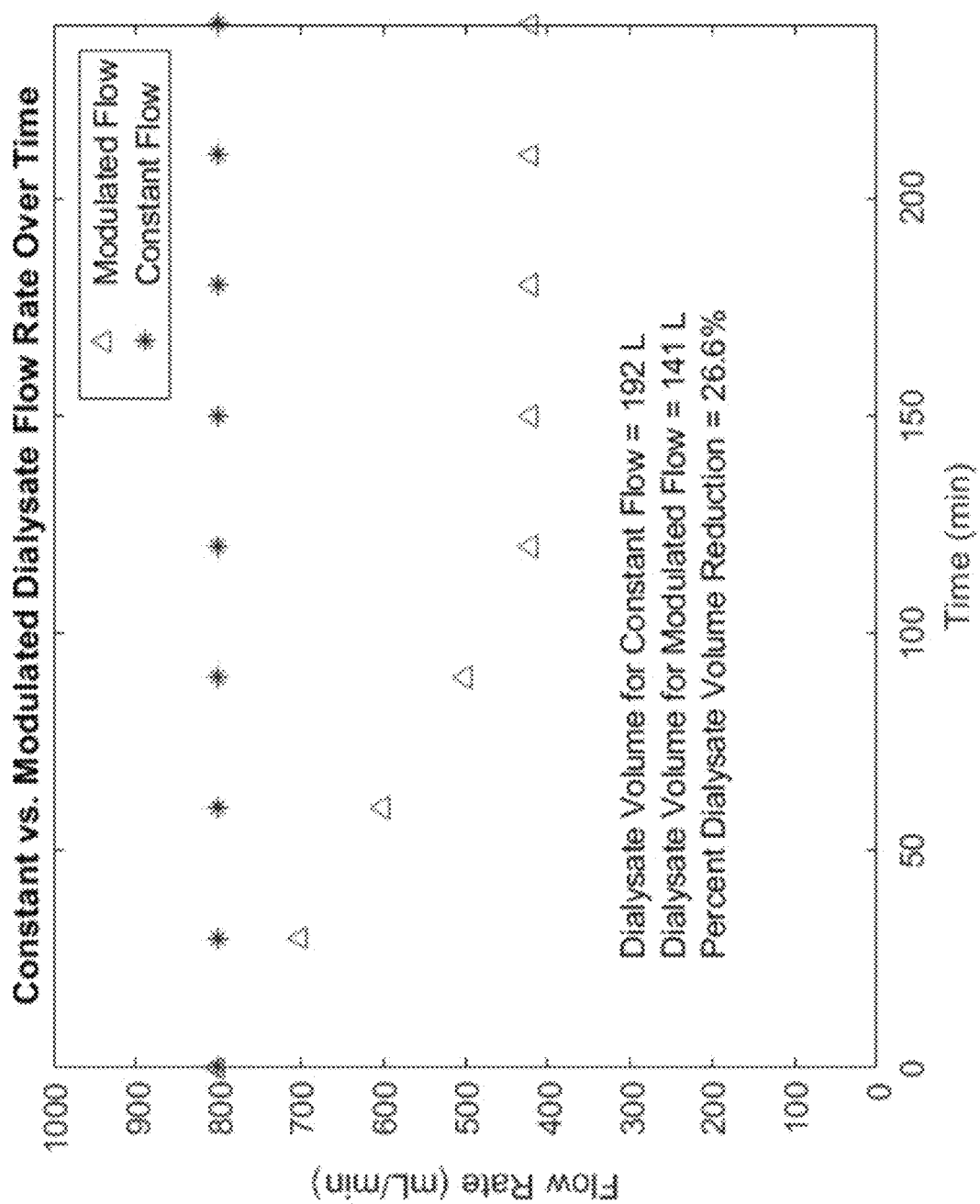
FIG. 19B is a graph comparing the flow rates of a constant flow system vs. a modulated flow system with a $Q_D$ decrease of 100 mL/min, according to embodiments.
Figure 20A:
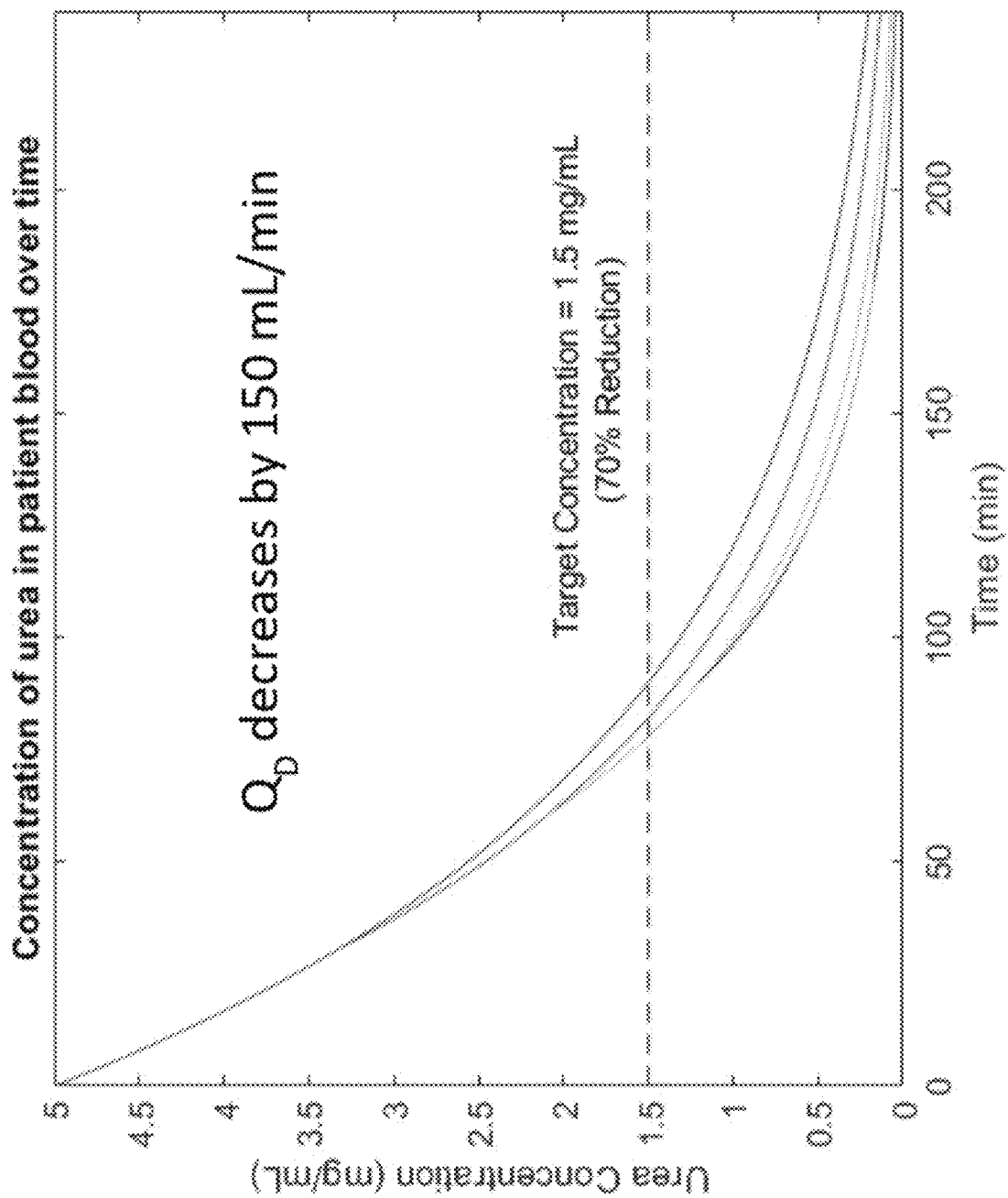
FIG. 20A is a graph depicting the concentration of urea in patient blood over time with a $Q_D$ degrease of 150 mL/min, according to an embodiment of the invention.
Figure 20B:
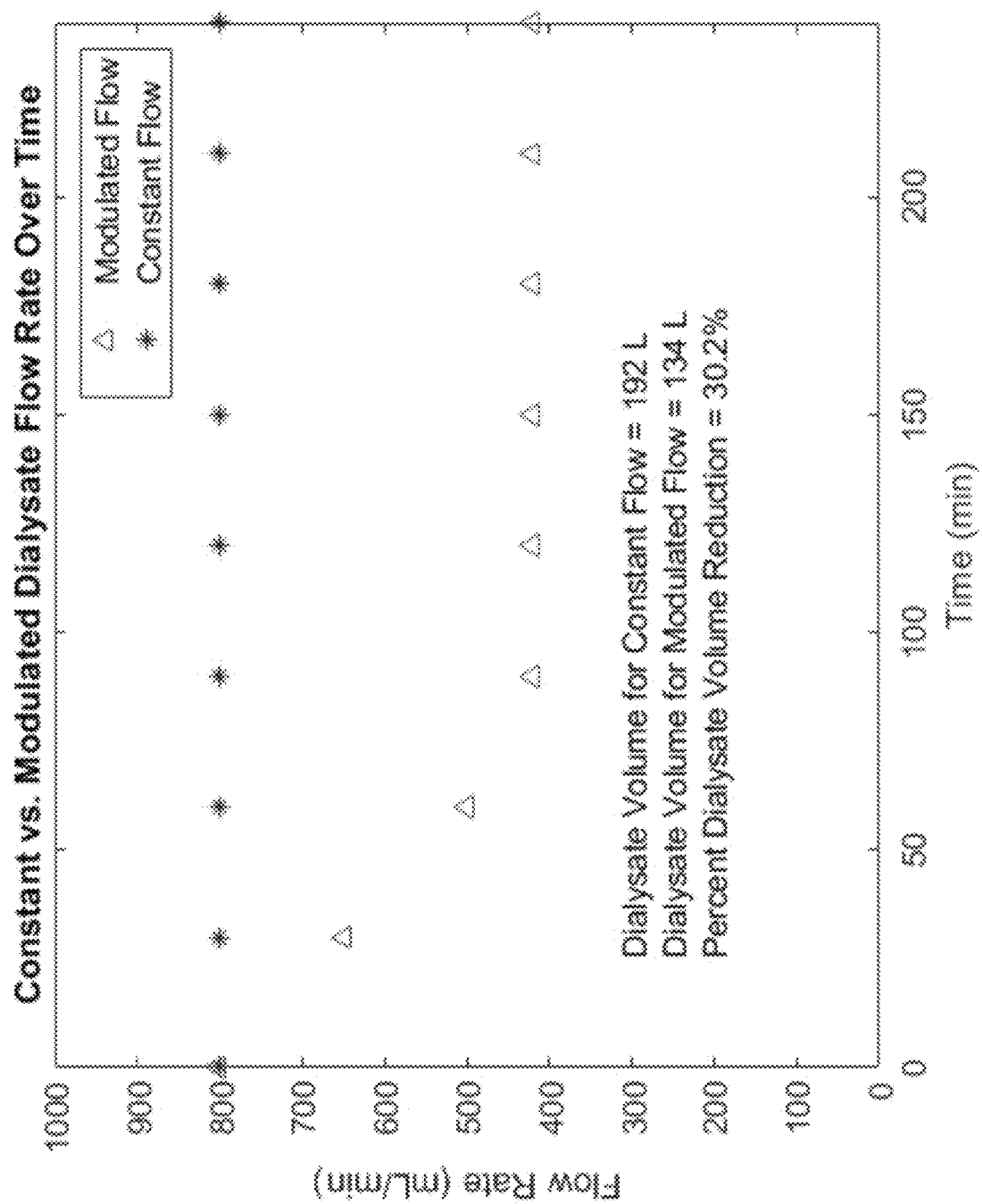
FIG. 20B is a graph comparing the flow rates of a constant flow system vs. a modulated flow system with a $Q_D$ decrease of 150 mL/min, according to embodiments.

The user interface for this system includes several starting parameters and a manual/auto switch that can be utilized by staff (FIG. 8). The starting parameters for typical treatments are: estimated treatment time (hours), sampling intervals (min) and the type of filter used for each treatment (drop down selection). The manual/auto switch is for staff to turn off communication protocols in the event that the treatment must be controlled manually. The user interface provides staff with relevant information on the molecular readings at various points during treatment or throughout the treatment. Two graphs will chart data points for measuring Urea in the waste vs. sampling time, and adjusted Dialysate flow rate vs. sampling time. The interface includes a gauge indicating how much of the Urea content has been reduced (treatment progress), a countdown to the next sampling time (min), and a total treatment time gauge (hours). A light in the interface panel indicates when a reading is being taken and locked fields display the last reading from the unit, and the current blood flow and dialysate flow rates, shown in FIG. 7.

Example

Figure 21:
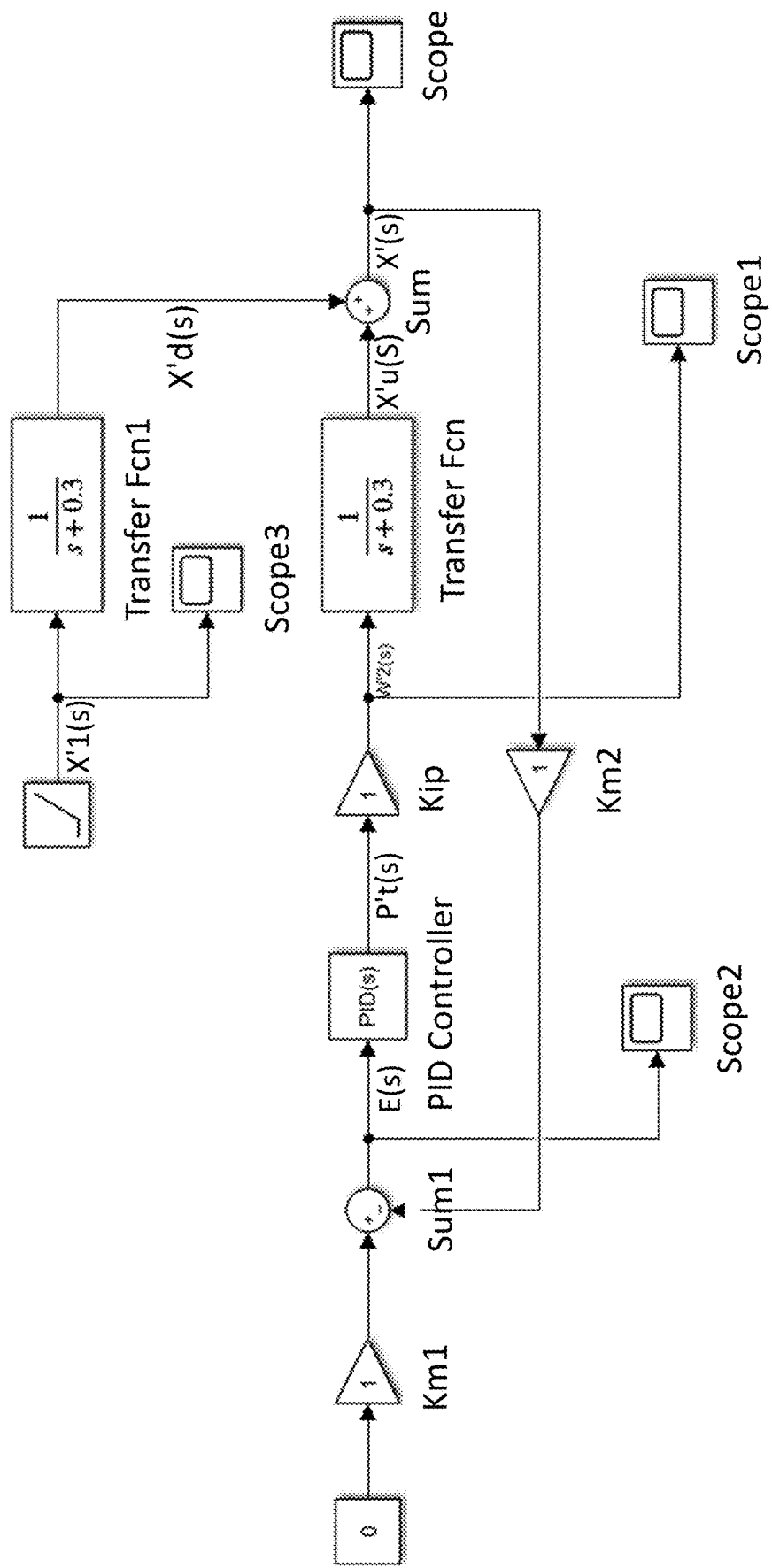
FIG. 21 is a scheme depicting the PID controller in Simulink.
Figure 22A:
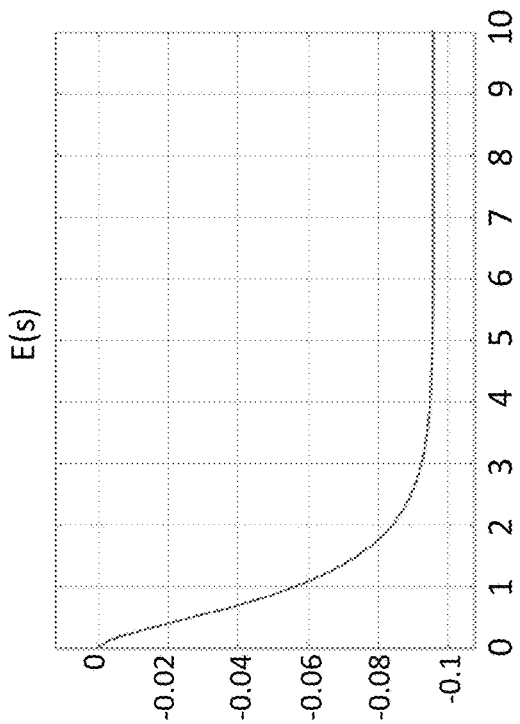
FIG. 22A is a graph showing instability of the PID controller with a proportional gain of 20.0, according to an embodiment of the invention.
Figure 22B:
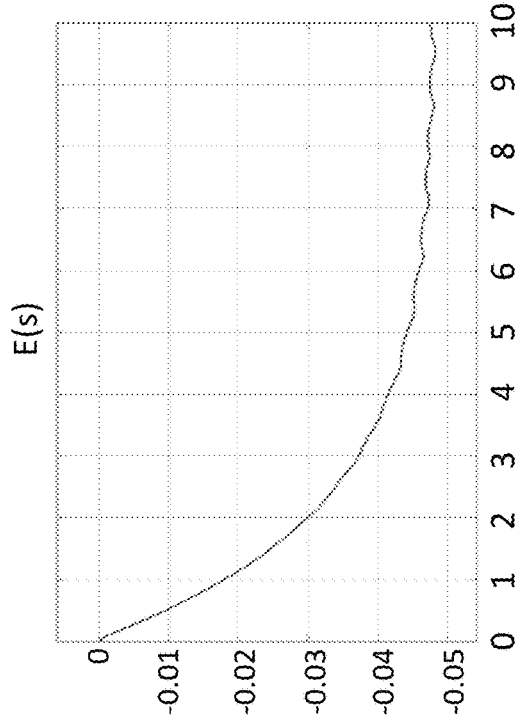
FIG. 22B is a graph showing stability of the PID controller with a proportional gain of 5.0, according to an embodiment of the invention.
Figure 22C:
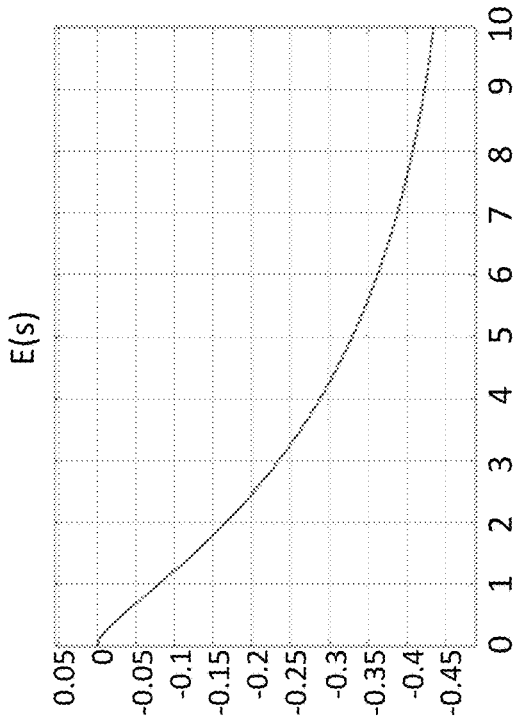
FIG. 22C is a graph showing lack of adjustment of the PID controller with a proportional gain of 4.0, according to an embodiment of the invention.
Figure 23A:
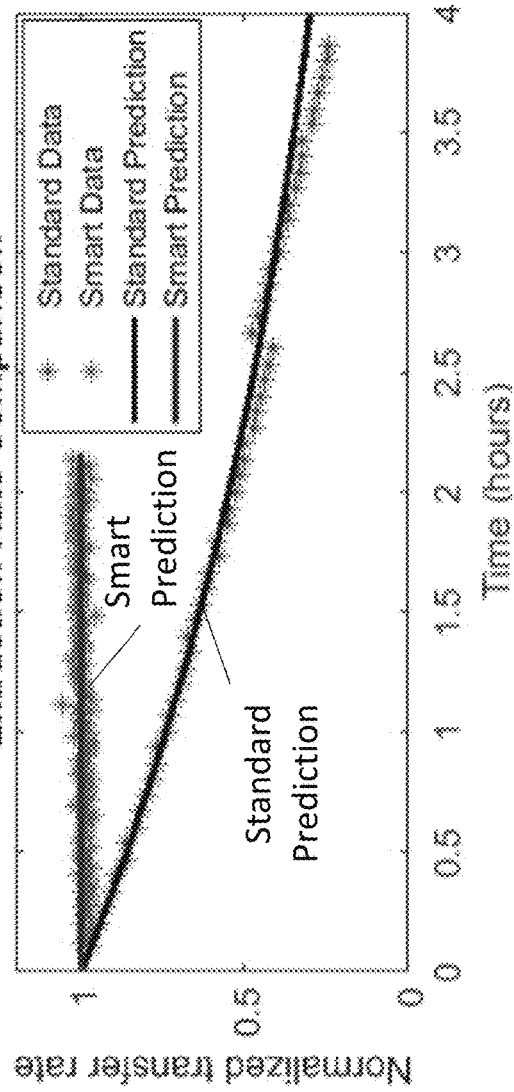
FIG. 23A is a graph comparing the extraction rate of an analyte using a standard prediction and using a smart prediction algorithm according to an embodiment of the invention.
Figure 23B:
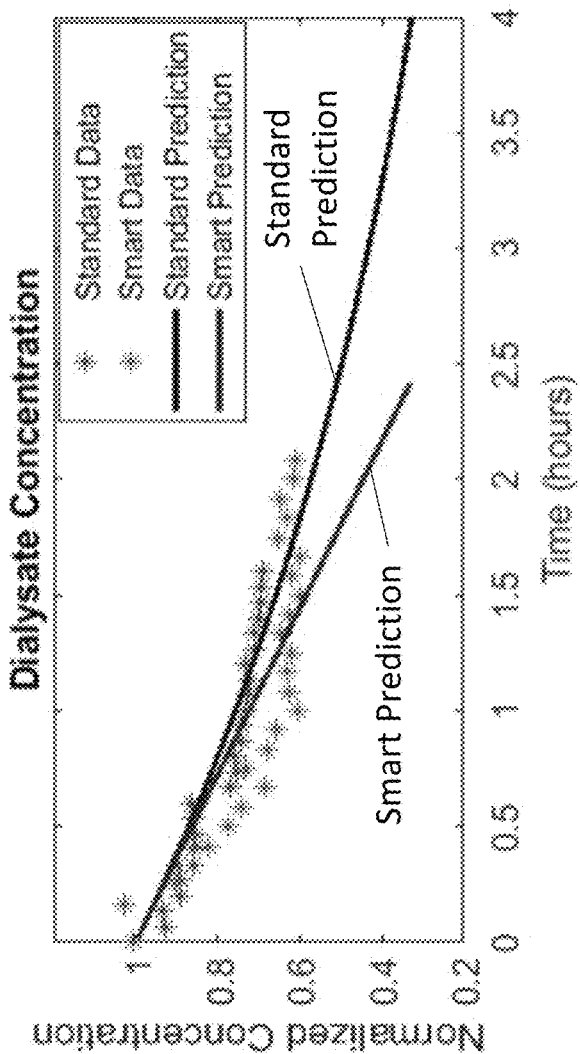
FIG. 23B is a graph comparing the concentration of an analyte over time using a standard prediction and using a smart prediction algorithm according to embodiments.
Figure 24:
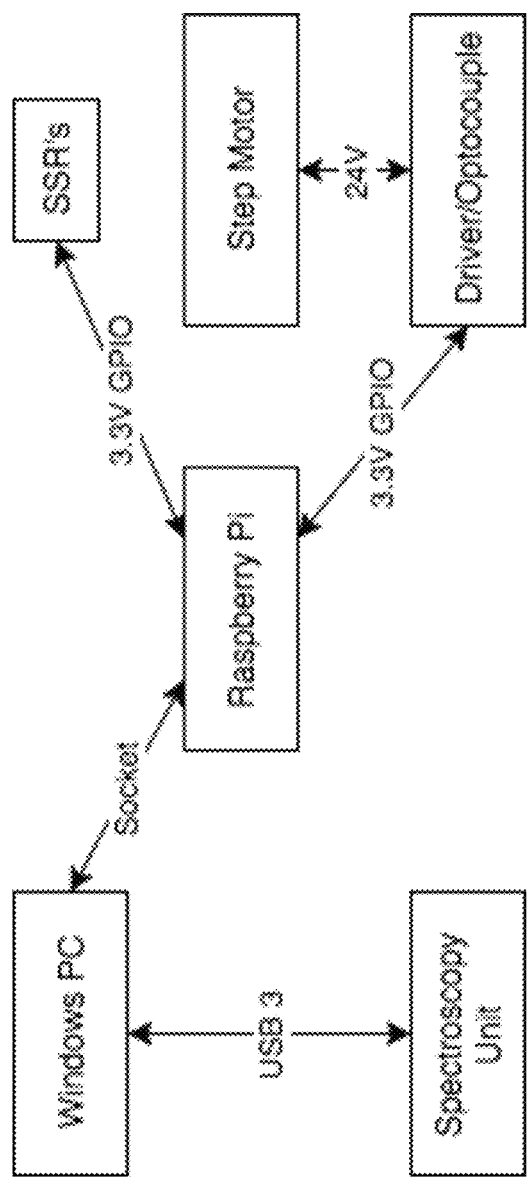
FIG. 24 is a diagram of the landmark components of the design according to an embodiment of the invention and the methods by which they are interconnected.
Figure 25:
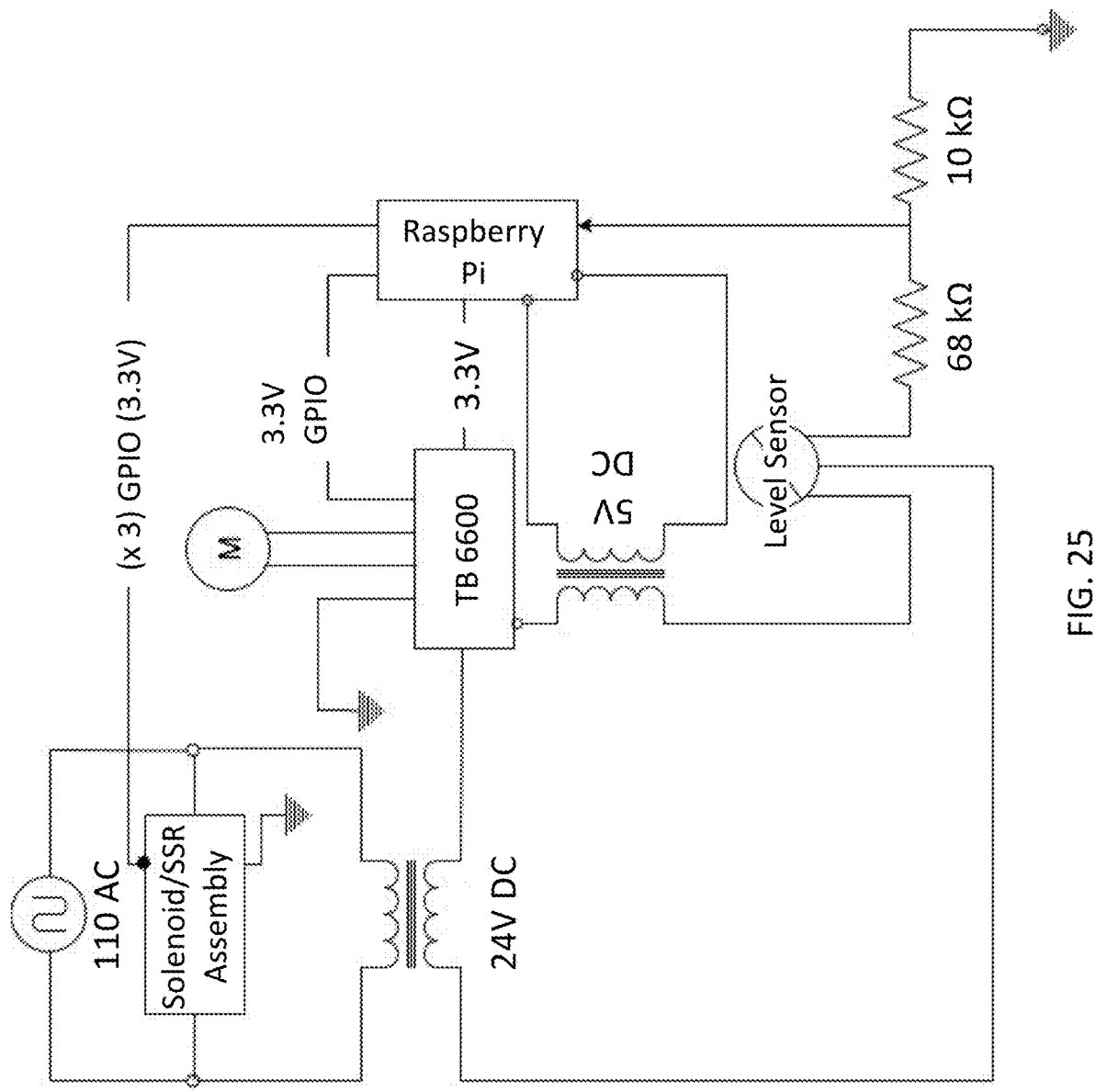
FIG. 25 is a diagram outlining the major electrical components utilized in a representative device designed to control dialysis flow rate.
Figure 26:
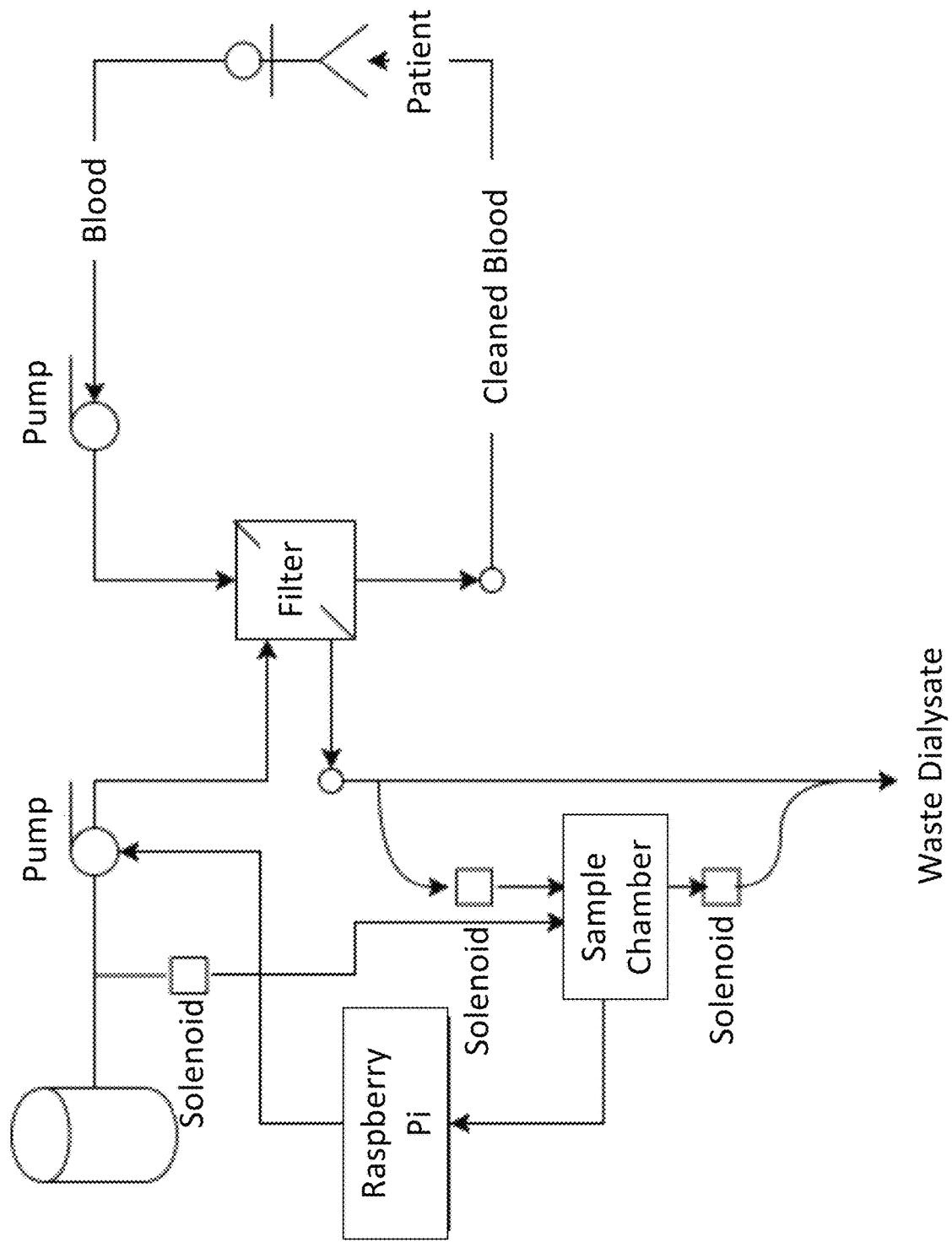
FIG. 26 is a diagram depicting the incorporation of a representative device designed to control dialysis flow rate into a hemodialysis system.
Figure 27:
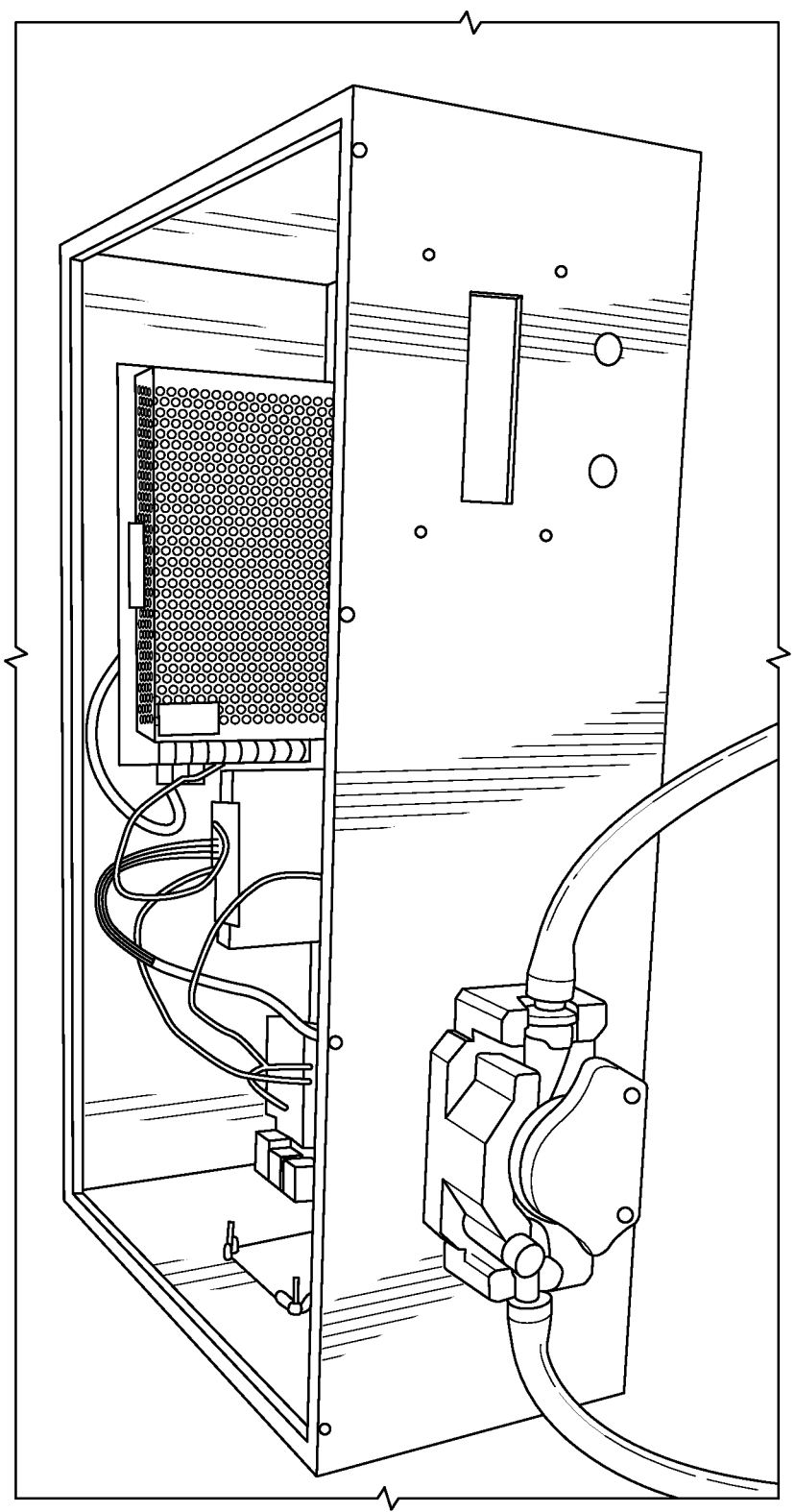
FIG. 27 is a photograph of a representative device designed to control dialysis flow rate according to embodiments of the invention, showing inter alia a peristaltic pump, Raspberry Pi, DC motor, and aluminum box housing.
Figure 28:
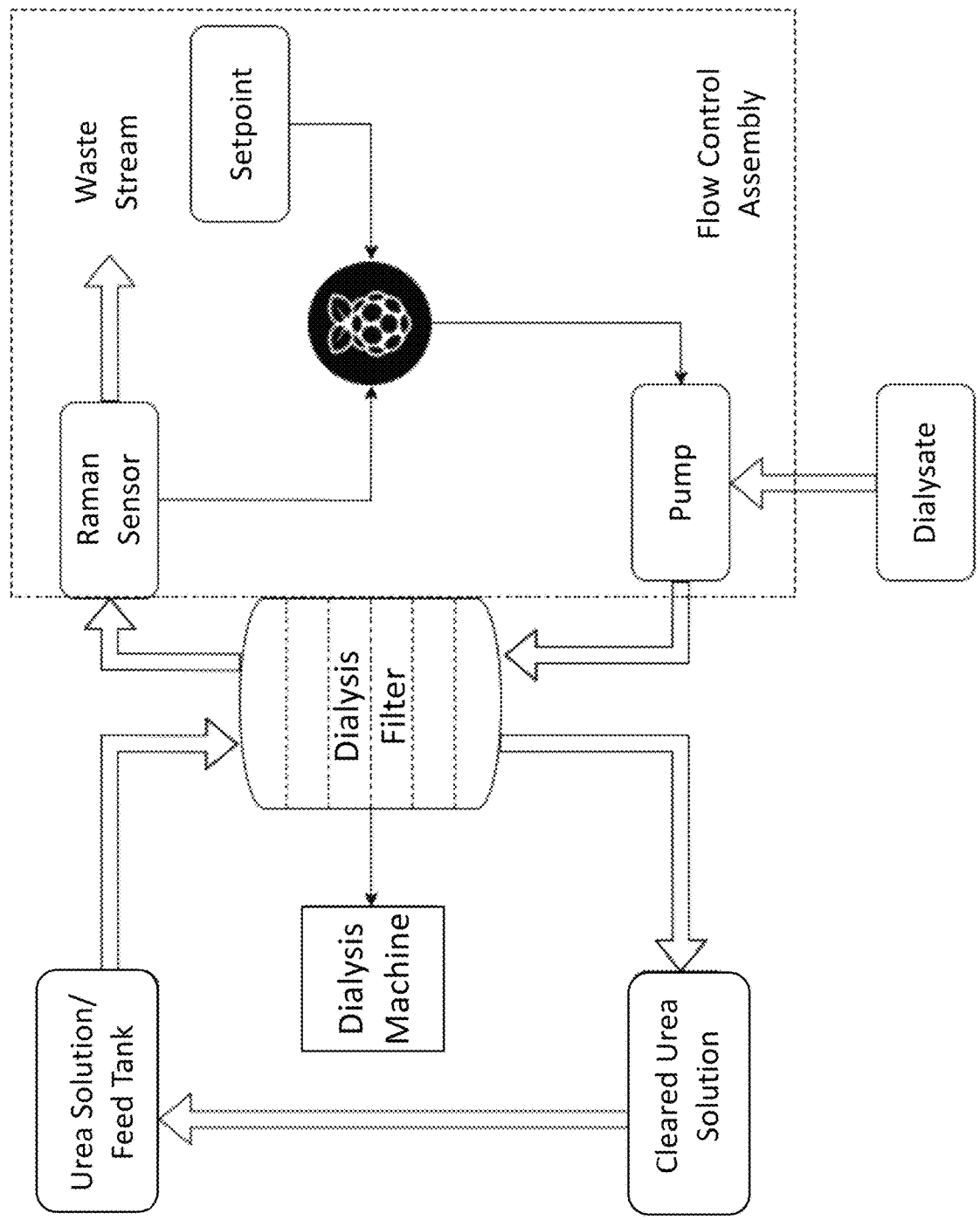
FIG. 28 is a diagram illustrating how a system can be integrated into the test environment, which utilizes a dialyzer filter and a urea solution to represent the patient's blood. Wide arrows represent fluid flow rate while thin arrows represent data flow.

The methods and technologies used to establish PID control of the dialysis flow line was through the use of several Python scripts and libraries, a Raspberry Pi microprocessor, a step-motor based peristaltic pump, and a Raman spectrophotometer (FIG. 24). Urea concentration in the waste dialysate line was monitored via spectroscopic data collected through the spectrophotometer. This data is then run through baselining algorithms and pre-processing on a Windows computer interfaced with the spectrophotometer. Following these steps, refined data is then passed through an INET socket connection to the Raspberry Pi. The Raspberry Pi used this data and Python-based PID control library to determine the optimal flow rate for the dialysate pump. The set point for these PID calculations was based on the lowest detectable urea concentration through the spectrophotometer, while the proportional, integral and derivative gain values were determined via a Simulink model (FIG. 21).

flow controller enclosure containing the functional components used to validate the design and the underlying theory that modulation of waste line flow could achieve water conservation while maintaining efficacy of solute extraction is shown in FIGS. 1-5.

Raman Spectroscopy was used to analyze samples from the waste dialysate line. At different time points, a sample would be collected and analyzed. The spectroscopy unit would provide spectra, where peak height corresponded to concentrations of different molecules. Although other analyte(s) can be analyzed, the molecule urea was the main molecule of focus due to its single, very distinct peak, and the fact that it is one of the main toxins filtered out of the patient's circulation during dialysis. It also shares a similar molecular size to other target molecules that pass through the dialyzer filter.

Figure 29:
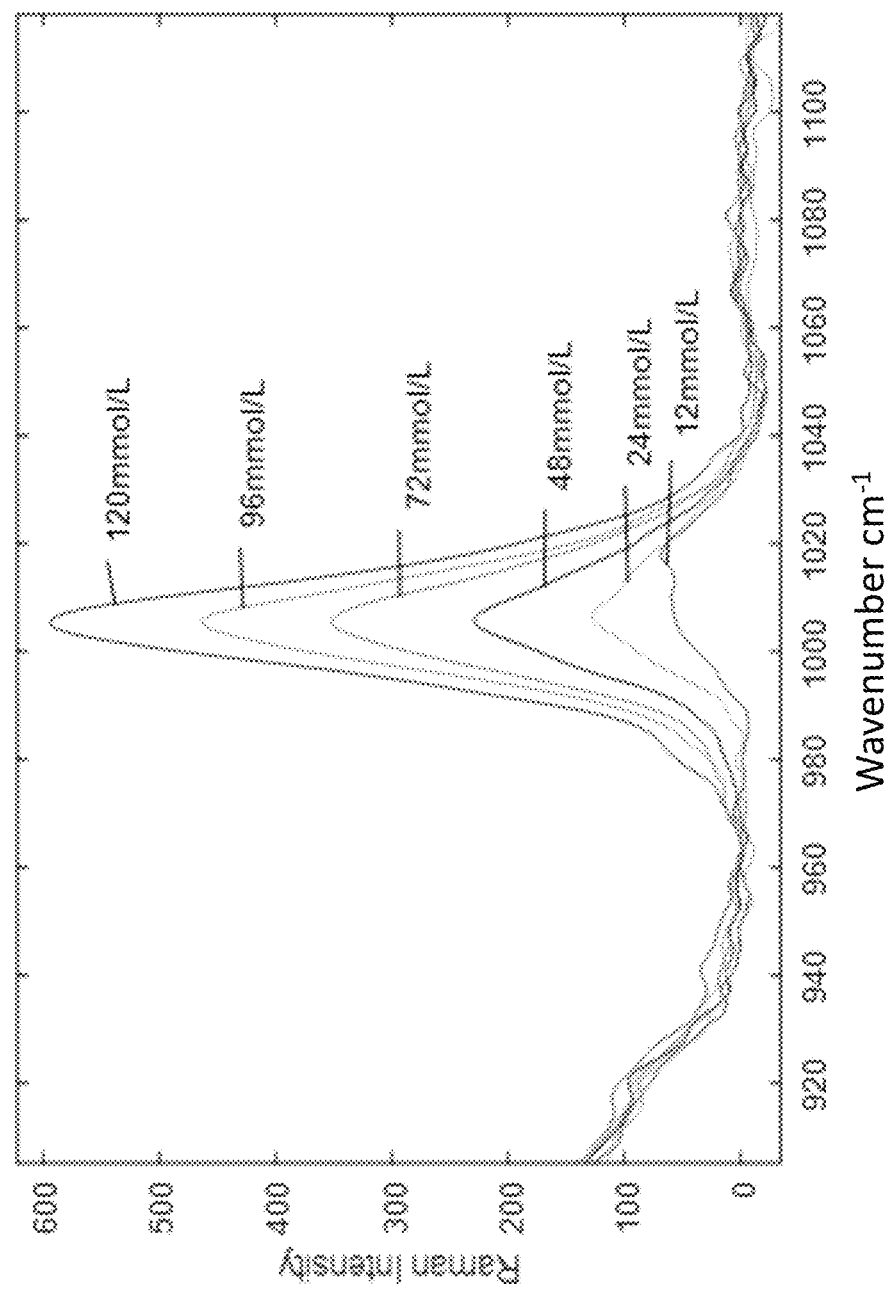
FIG. 29 is a graph showing urea peak height data and corresponding concentration seen by Raman spectroscopy.
Figure 30:
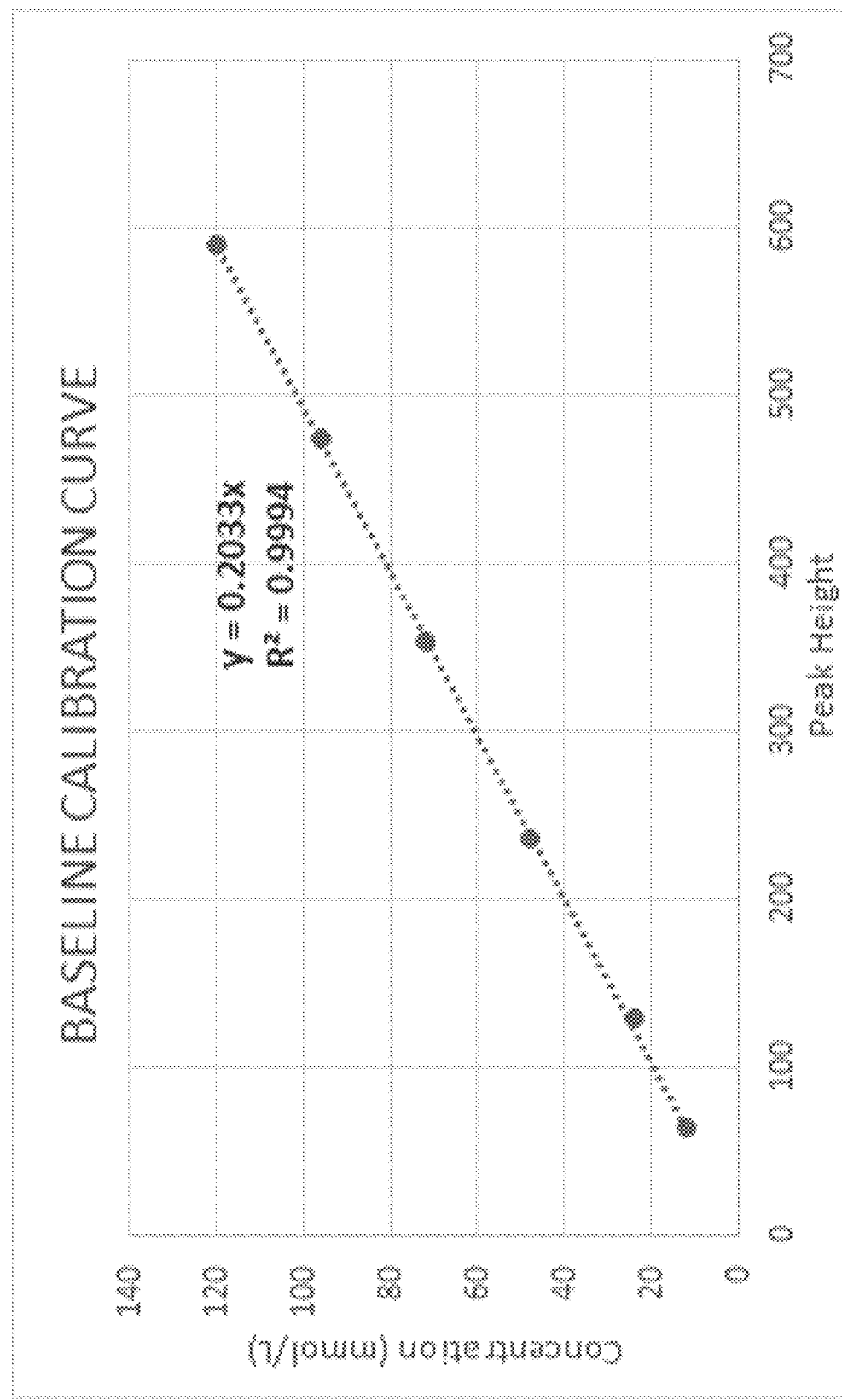
FIG. 30 is a graph showing the baseline calibration curve solved for using the urea concentration and peak height from FIG. 29.

The urea peak appeared at a wavenumber of 1003 cm$^{-1}$. To calculate unknown solute/analyte (e.g., urea) concentrations, a calibration curve was created using known concentrations and corresponding peak heights. The peak heights with corresponding urea concentrations are displayed in FIG. 29. Those values were used to create the calibration curve in FIG. 30. The slope of the calibration curve, 0.2033 mmol/L/Raman intensity, was then used to calculate all urea concentrations throughout the trials, as it had a direct correlation with the peak height data from the Raman.

Two tests were conducted to compare the water usage of a standard dialysis treatment and an improved water (di-

TABLE 1

Sample set of gain values test in PID controller.

| Proportional Gain | Integral Gain | Derivative Gain | Output scope (aim 0) | Error scope (aim 0) | Control after (min) | Error adjust after (min) | Comments |
|---|---|---|---|---|---|---|---|
| 20.0 | 10.0 | 0.50 | 0.1 | −0.048 | 1 | 8 | Instability |
| 5.0 | 5.0 | 0.05 | 0.1 | −0.093 | 2 | 4 | No Instability |
| 4.0 | 1.0 | 0.05 | 0.7 | −0.470 | 2 | 20 | Too long to adjust error |

This ideal flow rate was then converted into a variable frequency, constant duty cycle pulse width modulated (PWM) signal—outputted via a 3.3 VDC general purpose input/output (GPIO) pin. This PWM signal was used to rotate the pump head—where one pulse resulted in a partial rotation of the pump head. Therefore, higher rotation frequencies will yield higher flow rates and vice versa while maintaining precise control of the motor. Also necessary for the functionality of the design was a TB6600 step motor driver, a 110 VAC to 24 VDC transformer, and an array of solenoids/solid-state-relays (SSRs). The SSRs and solenoids were used to divert flow for sample collection, while the transformer and motor driver were used to supply current at appropriate voltages to the appropriate coils of the motor.

Figure 31:
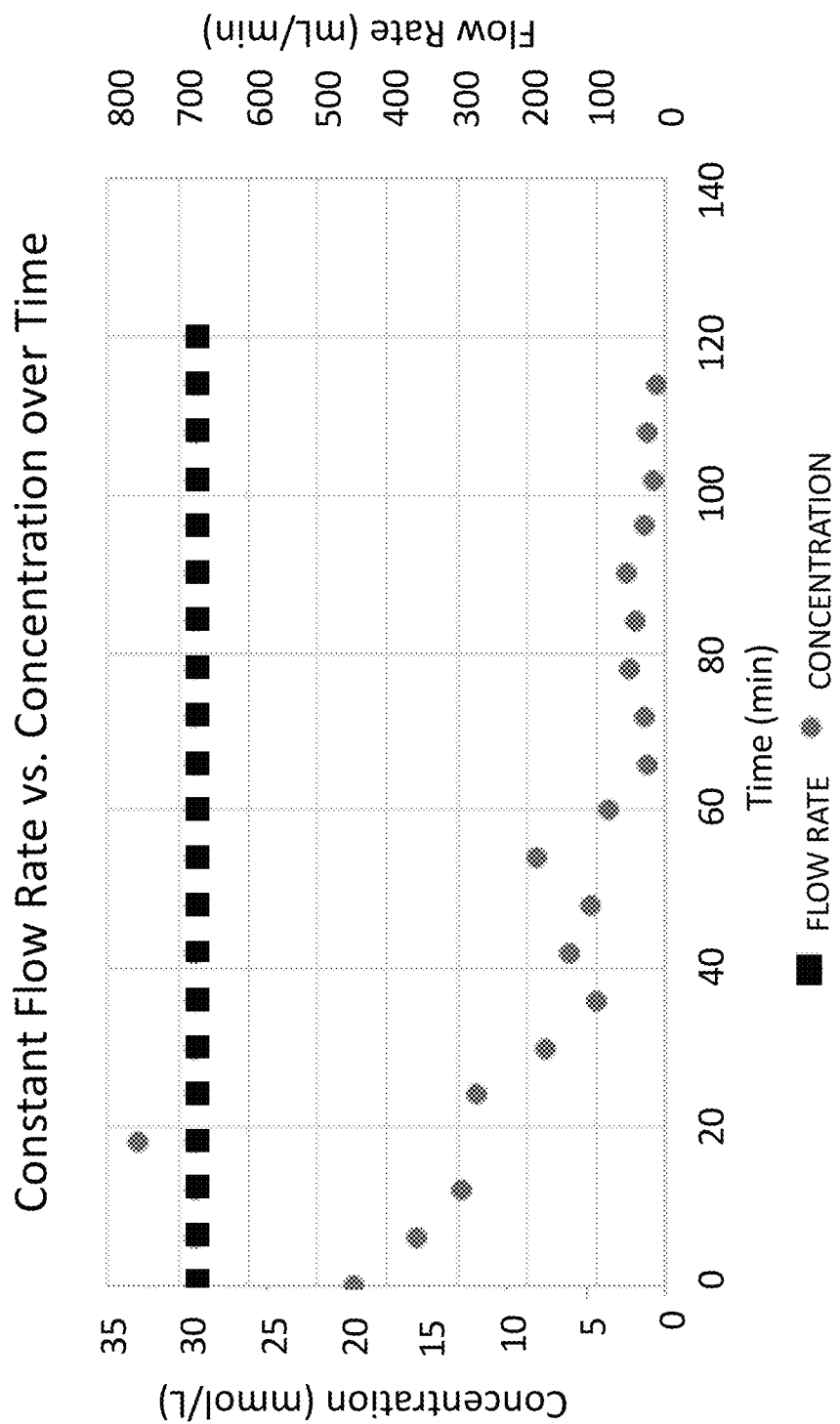
FIG. 31 is a graph showing urea concentration for uncontrolled flow rate test through dialyzer according to embodiments of the invention.
Figure 32:
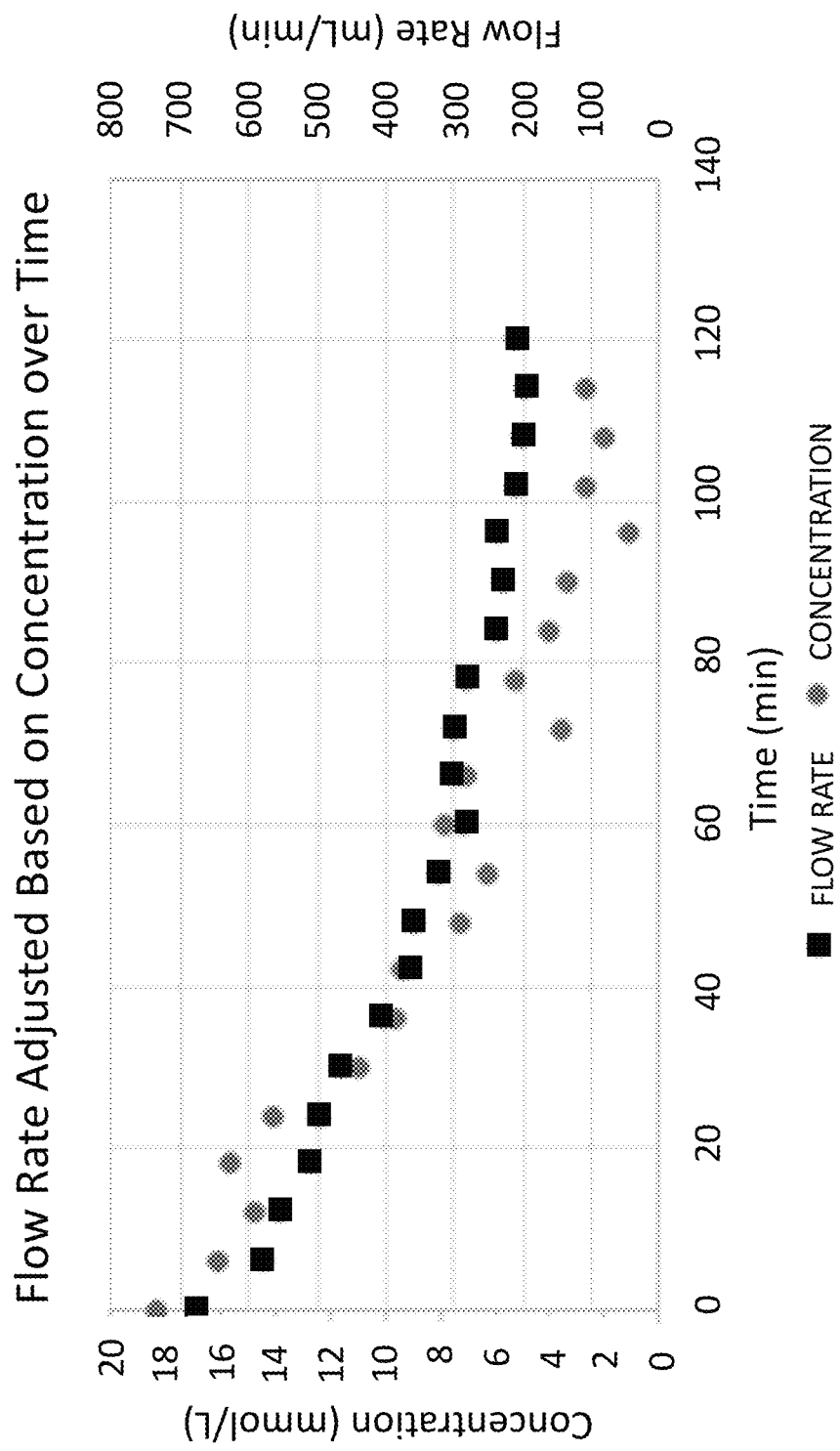
FIG. 32 is a graph showing urea concentration response for Proportional Integral Derivative (PID) controlled flow rate test through dialyzer.

The product that was produced and tested in simulation of hemodialysis was a prototype of the expected final product. All essential components of the design were validated with respect to functionality. Functional sampling chambers, SSR, and solenoid arrays can also be integrated into the systems. Additionally or alternatively, spectroscopic collections can be run through a secondary computer, while optimally this information could be input via the Raspberry Pi's USB ports. An embodiment of the waste dialysate line alysate)-conserving dialysis treatment employing our device. The first test was conducted at a constant flow rate of 675 mL/min throughout the entire two-hour simulated treatment, whereas, the second test was conducted with adjustment of flow rate based on urea concentration in the dialysate waste line. Both tests were started using simulated 'blood' made from 34.24 g of urea and 8 L of water, the 'blood' flow rate was kept at 450 mL/min, and samples were collected every six minutes. The samples for the constant flow rate were analyzed after testing, while the samples of the PID controlled testing were scanned semi-automatically after they were taken, in order to calculate urea concentration and adjust flow rate. The urea concentrations were plotted against time and flow rate, as shown in FIGS. 31 and 32.

The water usage of the two tests were recorded by using a 4 L Erlenmeyer flask. The difference in urea concentrations was calculated by taking the difference between the initial urea concentration and the final urea concentration. The water usage value and difference of urea concentration value are displayed in Table 2.

TABLE 2

Amount of urea reduced and water used during two-hour dialysis treatment.

|  | Differences in urea concentration (mmol/L) | Amount of water used (L) |
|---|---|---|
| Adjusted flow rate | 61.48 | 45.75 |
| Constant flow rate | 64.34 | 80.00 |

When using the PID controller during a two-hour dialysis treatment to adjust flow rate based on concentration, the blood urea concentration was reduced by 61.48 mmol/L using 45.75 L of water. Whereas, using a constant flow rate of 675 mmol/L during the two-hour treatment, the blood urea concentration was reduced by 64.34 mmol/L using 80.00 L of water. These values showed that the PID adjusted flow rate method used 42.81% less water than a typical dialysis.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A dialysis system comprising:
a base unit capable of performing dialysis treatment;
a Raman spectrometer operably coupled to a dialysate waste line of the base unit; and
a flow control unit in communication with a dialysate pump of the base unit for regulating flow of a dialysate;
wherein the flow control unit is configured to receive from the Raman spectrometer one or more Raman spectrum of at least a portion of the dialysate, process one or more of the Raman spectrum, determine the concentration of one or more analytes in the dialysate, and deliver a signal to the dialysate pump, modulating the flow of the dialysate.

2. The system of claim 1, wherein the base unit comprises at least:
one or more dialysate pump(s);
one or more dialysis filter(s);
one or more dialysate input line(s) for providing fresh dialysate to the dialysis filter(s); and
one or more dialysate waste line(s) for carrying used dialysate to waste.

3. The system of claim 1, further comprising a sampling chamber connected to the dialysate waste line.

4. The system of claim 2, further comprising one or more solenoid(s) for diverting dialysate flow for sample collection.

5. The system of claim 1, wherein the flow control unit is a proportional-integral-derivative controller.

6. The system of claim 1, wherein the flow control unit contains a Raspberry Pi microprocessor.

7. The system of claim 1, wherein the dialysate pump is a step-motor based peristaltic pump.

8. The system of claim 1, wherein the signal delivered to the dialysate pump is a variable frequency, constant duty cycle pulse width modulated signal.

9. The system of claim 1, further comprising one or more solenoid(s) and/or solid-state relay(s) to divert at least a portion of the dialysate flow to a sampling chamber for data collection.

10. The system of claim 9, wherein the system is configured such that the portion of the dialysate flow diverted for sample collection stops moving once inside the sampling chamber, a light emitting source of the Raman spectrometer is turned on, Raman spectra are collected, the light emitting source is turned off, and the dialysate flow resumes.

11. The system of claim 1, wherein one or more of the analyte(s) are chosen from urea, creatinine, or both.

12. The system of claim 10, wherein the flow control unit is programmed to terminate dialysis treatment when analyte concentration in blood is reduced by at least 70%, as calculated by one or more mass transfer model.

13. The system of claim 12, wherein the flow control unit is programmed to measure analyte peak from Raman spectrum, plug peak measurement into the mass transfer model, determine the new flow rate, and update the flow rate based on the mass transfer model.

14. The system of claim 1, further comprising a user interface.

15. A method for performing dialysis treatment, the method comprising:
providing one or more Raman spectrum(s) of a dialysate sample during a dialysis treatment;
determining a concentration of one or more analyte(s) present in the dialysate sample; and
modulating dialysate flow rate in a manner that provides an amount of one or more of the analyte(s) within a specified range.

16. The method of claim 15, wherein one or more of the analyte(s) are chosen from urea, creatinine, or both.

17. The method of claim 15, wherein the flow rate is modulated by keeping mass transfer rate constant.

18. A device for modulating dialysate flow rate, the device comprising:
a Raman spectrometer in operable communication with a dialysate waste line of a dialysis system;
a dialysate pump for moving a dialysate through the dialysate system; and
a flow control unit in operable communication with the dialysate pump for modulating flow rate of a flow of a dialysate through the dialysis system;

wherein the flow control unit is configured to:
(i) receive from the Raman spectrometer one or more Raman spectrum(s) of the dialysate exiting a dialysis filter of the dialysis system,
(ii) process the Raman spectrum,
(iii) determine a concentration of one or more analyte(s) in the dialysate exiting the dialysis filter of the dialysis system, and
(iv) deliver a signal to the dialysate pump, to modulate the dialysate flow rate.

19. The device of claim 18, further comprising a sampling chamber and one or more solenoid(s) and/or solid-state relay(s) to divert the dialysate flow to the sampling chamber.

20. The device of claim 18, further comprising data storage for gathering patient profiles.

* * * * *